(12) United States Patent
Rubinstenn et al.

(10) Patent No.: US 7,634,103 B2
(45) Date of Patent: Dec. 15, 2009

(54) ANALYSIS USING A THREE-DIMENSIONAL FACIAL IMAGE

(75) Inventors: Gilles Rubinstenn, Paris (FR); Daniela Giacchetti, Paris (FR); Francis Pruche, Senlis (FR)

(73) Assignee: L'Oreal S.A., Paris (FR)

( * ) Notice: Subject to any disclaimer, the term of this patent is extended or adjusted under 35 U.S.C. 154(b) by 729 days.

(21) Appl. No.: 10/024,615

(22) Filed: Dec. 21, 2001

(65) Prior Publication Data

US 2003/0063794 A1 Apr. 3, 2003

Related U.S. Application Data

(60) Provisional application No. 60/325,559, filed on Oct. 1, 2001.

(51) Int. Cl.
*G06K 9/00* (2006.01)
*G09G 5/00* (2006.01)

(52) U.S. Cl. .................. 382/100; 382/118; 382/154; 345/619

(58) Field of Classification Search .............. 382/100, 382/128, 154, 118; 703/6; 345/619; 348/77
See application file for complete search history.

(56) References Cited

U.S. PATENT DOCUMENTS

| | | | |
|---|---|---|---|
| 5,751,829 A | 5/1998 | Ringland et al. | |
| 5,825,941 A * | 10/1998 | Linford et al. | ............ 382/294 |
| 5,930,769 A | 7/1999 | Rose | |
| 6,081,611 A | 6/2000 | Linford et al. | |
| 6,091,836 A | 7/2000 | Takano et al. | |
| 6,215,498 B1 | 4/2001 | Filo et al. | |
| 6,260,024 B1 | 7/2001 | Shkedy | |
| 6,283,858 B1 | 9/2001 | Hayes, Jr. et al. | |
| 6,293,284 B1 | 9/2001 | Rigg | |
| 6,320,583 B1 | 11/2001 | Shaw et al. | |
| 6,362,850 B1 | 3/2002 | Alsing et al. | |
| 6,377,745 B2 | 4/2002 | Akiba et al. | |
| 6,427,022 B1 | 7/2002 | Craine et al. | |
| 6,453,052 B1 * | 9/2002 | Kurokawa et al. | .......... 382/100 |
| 6,502,583 B1 | 1/2003 | Utsugi | |
| 6,504,546 B1 * | 1/2003 | Cosatto et al. | .............. 345/473 |
| 6,526,158 B1 | 2/2003 | Goldberg | |
| 6,571,003 B1 | 5/2003 | Hillebrand et al. | |

(Continued)

FOREIGN PATENT DOCUMENTS

EP      0 226 959      7/1987

(Continued)

OTHER PUBLICATIONS

Machine translation of JP 2001-104050.*

(Continued)

*Primary Examiner*—John B Strege
(74) *Attorney, Agent, or Firm*—Finnegan, Henderson, Farabow, Garrett & Dunner, LLP

(57) ABSTRACT

Disclosed methods and systems related to enabling an analysis using a three-dimensional facial image. One of the methods involves facilitating construction of a three-dimensional facial image using at least captured image of a subject's face. The method also involves facilitating a simulation of use of an aesthetic feature on the three-dimensional facial image and/or processing of the three-dimensional facial image to enable a beauty analysis.

41 Claims, 22 Drawing Sheets

INITIAL SIMULATED
FACIAL IMAGE

SIMULATED
FACIAL IMAGE WITH
AESTHETIC FEATURES

U.S. PATENT DOCUMENTS

| | | | |
|---|---|---|---|
| 6,692,127 | B2* | 2/2004 | Abitbol et al. ............... 351/227 |
| 6,792,401 | B1* | 9/2004 | Nigro et al. .................... 703/6 |
| 2001/0011818 | A1 | 8/2001 | Dockery et al. |
| 2001/0014868 | A1 | 8/2001 | Herz et al. |
| 2001/0037191 | A1* | 11/2001 | Furuta et al. ................... 703/6 |
| 2002/0024528 | A1 | 2/2002 | Lambertsen |
| 2002/0054714 | A1 | 5/2002 | Hawkins et al. |
| 2002/0064302 | A1 | 5/2002 | Massengill |
| 2003/0014324 | A1 | 1/2003 | Donovan et al. |
| 2003/0164955 | A1* | 9/2003 | Vinas et al. .................. 358/1.2 |

FOREIGN PATENT DOCUMENTS

| | | | |
|---|---|---|---|
| EP | 1 030 267 | | 8/2000 |
| EP | 1 134 701 | | 9/2001 |
| EP | 1 169 964 | | 1/2002 |
| JP | 6-118349 | | 4/1994 |
| JP | 2000-315262 | | 11/2000 |
| JP | 2001104050 | * | 4/2001 |
| JP | 2001-52108 | | 11/2001 |
| WO | WO 97/29441 | * | 8/1997 |
| WO | WO 98/20458 | | 5/1998 |
| WO | WO 99/23609 | | 5/1999 |
| WO | WO 00/33271 | | 6/2000 |
| WO | WO 00/76398 | | 12/2000 |
| WO | WO 01/04838 | | 1/2001 |
| WO | WO 01/04840 | | 1/2001 |
| WO | WO 01/18674 | | 3/2001 |
| WO | WO 01/20517 | | 3/2001 |
| WO | WO 01/57771 | | 8/2001 |
| WO | WO 01/77976 | | 10/2001 |
| WO | WO 01/80122 | | 10/2001 |
| WO | WO 01/87245 | | 11/2001 |
| WO | WO 01/91600 | | 12/2001 |
| WO | WO 01/91601 | | 12/2001 |
| WO | WO 02/03232 | | 1/2002 |
| WO | WO 02/05249 | | 1/2002 |
| WO | WO 02/37421 | | 5/2002 |

OTHER PUBLICATIONS

Official English Translation of JP2001104050, Naigaishi (PN=13104050).*
Yin Wu, et al., "A Plastic-Visco-Elastic Model for Wrinkles in Facial Animation and Skin Aging", MIRALab, 1998.
Catherine Pelachaud, et al., "Final Report to NSF of the Standards for Facial Animation Workshop", the Institute for Research in Cognitive Science, University of Pennsylvania, IRCS Report 94-21, Nov. 1994, pp. 1-62.
U.S. Appl. No. 10/024,354; Title: Methods and Systems for Predicting and/or Tracking Changes in External Body Conditions Inventor(s): Gilles Rubinstenn et al. filed Dec. 21, 2001 Preliminary Amendment Filed: Apr. 22, 2002.
U.S. Appl. No. 10/024,333; Title: Methods and Systems for Generating a Prognosis Inventor(s): Gilles Rubinstenn et al. filed Dec. 21, 2001 Preliminary Amendment Filed: Apr. 22, 2002.
U.S. Appl. No. 10/024,622; Title: Historical Beauty Record Inventor(s): Daniela Giacchetti et al. U.S. filing Date: Dec. 21, 2001 Preliminary Amendement Filed: Apr. 22, 2002.
U.S. Appl. No. 10/024,332; Title: Identification and Presentation of Analogous Beauty Case Histories Inventor(s): Gilles Rubinstenn filed Dec. 21, 2001 Preliminary Amendement Filed: Apr. 22, 2002.
U.S. Appl. No. 10/024,481; Title: Interactive Beauty Analysis Inventor(s): Gilles Rubinstenn et al. filed Dec. 21, 2001 Preliminary Amendment Filed: Apr. 22, 2002.
U.S. Appl. No. 10/024,495; Title: Feature Extraction in Beauty Analysis Inventor(s): Gilles Rubinstenn et al. filed Dec. 21, 2001 Preliminary Amendment Filed: Apr. 22, 2002.
U.S. Appl. No. 10/024,353; Title: Simulation of an Aesthetic Feature on a Facial Image Inventor(s): Daniela Giacchetti et al. filed Dec. 21, 2001 Preliminary Amendment Filed: Apr. 22, 2002.
U.S. Appl. No. 10/024,496; Title: Beauty Advisory System and Method Inventor(s): Gilles Rubinstenn et al. filed Dec. 21, 2001 Preliminary Amendment Filed: Apr. 22, 2002.
U.S. Appl. No. 10/024,620; Title: Virtual Beauty Consultant Inventor(s): Daniela Giacchetti et al. filed Dec. 21, 2001 Preliminary Amendment Filed: Apr. 22, 2002.
U.S. Appl. No. 10/024,334; Title: Calibrating Image Capturing Inventor(s): Gilles Rubinstenn filed Dec. 21, 2001 Preliminary Amendment Filed: Apr. 22, 2002.
U.S. Appl. No. 10/024,616; Title: Use of Artificial Intelligence in Providing Beauty Advice Inventor(s): Jerome Peyrelevade filed Dec. 21, 2001 Preliminary Amendment Filed: Apr. 22, 2002.
U.S. Appl. No. 10/024,352; Title: Shop-In-Shop Website Construction Inventor(s): Jerome Peyrelevade et al. filed Dec. 21, 2001.
U.S. Appl. No. 10/024,619; Title: Early Detection of Beauty Treartment Progress Inventor(s): Francis Pruche et al. filed Dec. 21, 2001 Preliminary Amendment Filed: Apr. 22, 2002.
U.S. Appl. No. 10/024,356; Title: Cosmetic Affinity Indexing Inventor(s): Daniela Giacchetti et al. filed Dec. 21, 2001.
U.S. Appl. No. 10/024,621; Title: Systems and Methods for Providing Beauty Guidance Inventor(s): Daniela Giacchetti et al. filed Dec. 21, 2001 Preliminary Amendment Filed: Apr. 22, 2002.
U.S. Appl. No. 10/024,355; Title: Methods and Systems Involving Simulated Application of Beauty Product Inventor(s): Jerome Peyrelevade et al. filed Dec. 21, 2001 Preliminary Amendment Filed: Apr. 22, 2002.
U.S. Appl. No. 10/024,351; Title: Customized Beauty Tracking Kit Inventor(s): Gilles Rubinstenn et al. filed Dec. 21, 2001 Preliminary Amendment Filed: Apr. 22, 2002.
U.S. Appl. No. 10/024,482; Title: Body Image Templates with Pre-Applied Beauty Products Inventor(s): Daniela Giacchetti filed Dec. 21, 2001 Preliminary Amendment Filed: Apr. 22, 2002.
U.S. Appl. No. 10/024,651; Title: Image Capture Method Inventor(s): Gilles Rubinstenn filed Dec. 21, 2001 Preliminary Amendment Filed: Apr. 22, 2002.
U.S. Appl. No. 10/024,480; Title: Body Image Enhancement Inventor(s): Gilles Rubinstenn et al. filed Dec. 21, 2001 Preliminary Amendment Filed: Apr. 22, 2002.
U.S. Appl. No. 10/024,034; Title: Devices and Methods for Enabling Evaluation of Typological Characteristics of External Body Portions, and Related Devices Inventor(s): Roland Bazin filed Dec. 21, 2001.
Notice of Rejection issued Jan. 17, 2006 by Japanese Patent Office in counterpart application JP No. 2002-288305.
Nobori et al., Image Synthesis System Using 3D Model-Based Coding—Simulates Facial Expressions and Aging, IEEE, 1992, pp. 394-395.

* cited by examiner

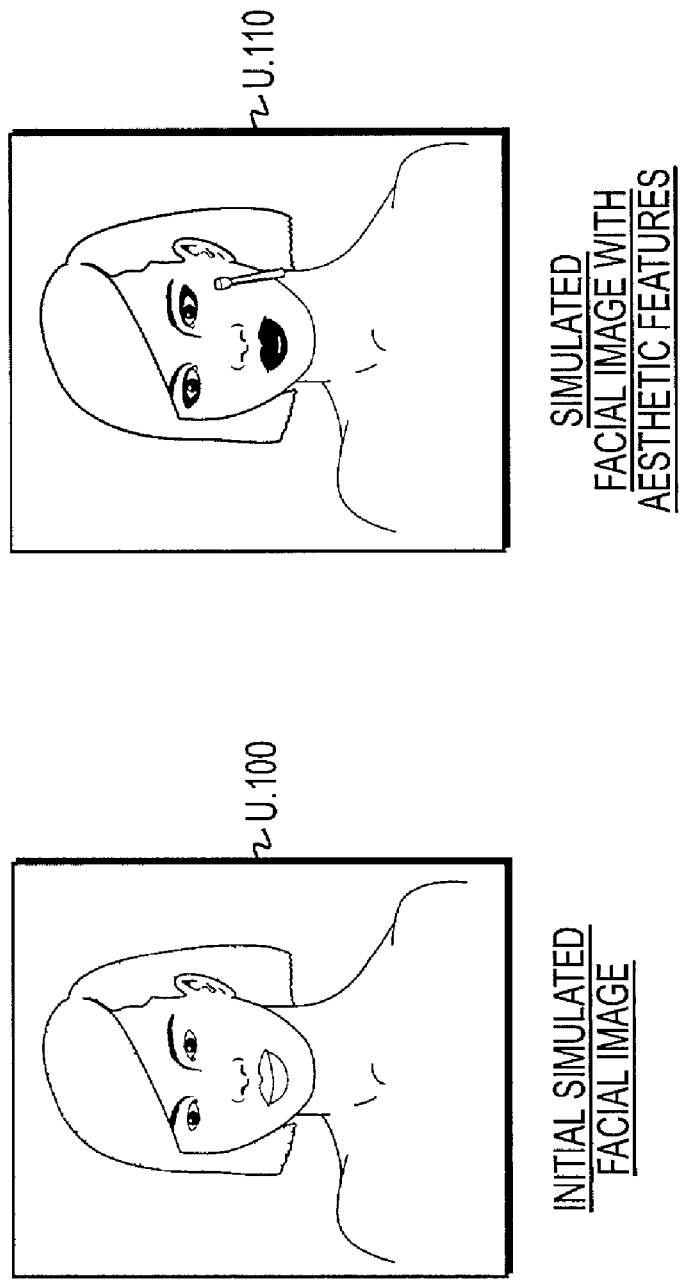
Figure 3A — INITIAL SIMULATED FACIAL IMAGE (U.100)
Figure 3B — SIMULATED FACIAL IMAGE WITH AESTHETIC FEATURES (U.110)

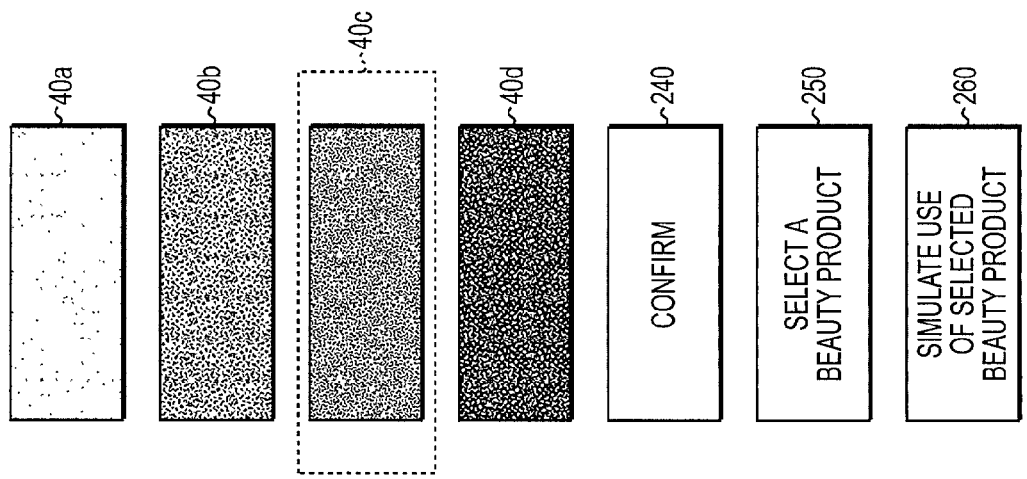
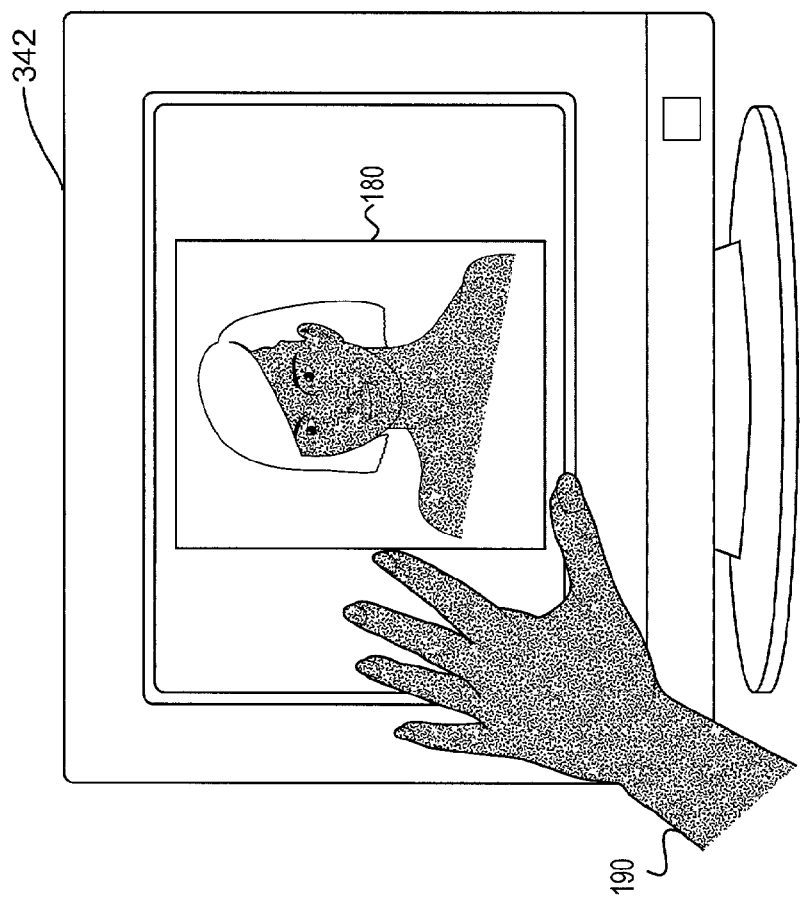
Figure 7

ANALYSIS USING A THREE-DIMENSIONAL FACIAL IMAGE

This application claims priority to U.S. provisional application No. 60/325,559, filed Oct. 1, 2001.

BACKGROUND OF THE INVENTION

1. Field of the Invention

The invention relates to methods, combinations, apparatuses, and systems involving one or more facial images. In another respect, the invention may involve a beauty analysis using a facial image.

2. Description of Related Art

For many beauty product consumers, cosmetic counters at retail establishments, such as department stores, provide an ideal mechanism for evaluating products. In this environment, consumers can try on a variety of products, test combinations of products, and determine which products and product combinations are most aesthetically pleasing. As a result, the cosmetic counter experience is a powerful tool not only for the consumer, but also as a mechanism for consummating sales.

Yet the conventional cosmetic counter experience has its drawbacks. It tends to require labor intensive one-on-one interaction with a beauty consultant. And, even when the consumer is left to her own devices, the process of applying or otherwise using beauty products, such makeup, is relatively time consuming. As a result, hurried consumers may avoid the cosmetic counter.

With the advent of electronic commerce, many web portals now offer beauty products for sale. This permits consumers to shop at their convenience even during hours when retail establishments are traditionally closed for business. Yet, the inability to physically test products and combinations of products may make some consumers reluctant to purchase cosmetics online.

SUMMARY OF A FEW ASPECTS OF THE INVENTION

In one exemplary aspect, the invention may provide at least some simulation of the cosmetic counter experience, allowing consumers to virtually apply beauty products on a facial image. Depending on how the invention is implemented, this may expedite the beauty product selection process and permit consumers to shop from a wide variety of locations during hours when traditional stores are closed, for example. Alternatively (or in addition), the virtual application of beauty products may impart the ability to expeditiously test products and/or provide some indication of how certain beauty products might impact an individual's future appearance.

Although certain aspects of the present invention are discussed in the context of beauty products and/or beauty analysis, it should be understood that the invention is not so limited and that some aspects of the invention could be used in other fields.

In one aspect of the invention, there is a method of enabling simulated use of an aesthetic feature on a simulated facial image. The method includes enabling an individual to construct a simulated facial image using a facial construction computer program. The facial construction computer program may permit the individual to select a head, eyes, nose, lips, ears, and/or eye brows. The method may also include enabling the simulated facial image to be displayed on a display device, and enabling the individual to select an aesthetic feature. The method may further include enabling the individual to simulate use of the selected aesthetic feature on the simulated facial image and to view on the display device an alteration of the simulated facial image having the simulated aesthetic feature.

In another aspect, there is a method of enabling an analysis using a three-dimensional facial image. The method includes facilitating construction of a three-dimensional facial image using at least one captured image of a subject's face. The method further includes facilitating a simulation of use of an aesthetic feature on the three-dimensional facial image and/or processing of the three-dimensional facial image to enable a beauty analysis.

In yet another aspect, there is a method of enabling a beauty analysis. The method includes facilitating display, on a display device, of a plurality of templates. As used herein, the term "template" refers to a representation, such as an image, that is reflective of subject matter that may be incorporated into a facial image. At least some of the templates are representative of a portion of a face having a simulation of use of a beauty product. The method also includes enabling selection of one or more of the displayed templates. The method further includes facilitating display, on the display device, of a simulated facial image including at least one displayed facial portion having a simulation of use of a beauty product, wherein the displayed facial portion having a simulation corresponds to the selected template(s).

According to another aspect of the invention, a method may involve recommending at least one beauty product complementary to a recommended/selected product. Such a method may include causing at least one query to be presented to a subject, and selecting a first beauty product based on the subject's response to the query. The method may further involve enabling a display, on a display device, of a simulated use of the first beauty product on a representative facial image and receiving from the subject an indication as to whether the first beauty product is acceptable. If so, the method may involve selecting at least one second beauty product complementary with the first beauty product.

Another aspect consistent with the invention, may include a method of enabling color-calibrating of a self-image for use in simulating a beauty product use. Such a method may include prompting a subject to capture, using an image capture device, an image of a body region of the subject and prompting the subject to compare a color of the displayed image with an actual color of the subject's body region. If the subject perceives a difference, the method may further involve enabling color-calibration of the image.

In accordance with another aspect of the invention, a method of enabling a beauty analysis may include instructing a subject on how to record at least one images of the subject's face. The method may further involve facilitating the conversion of at least one image into a three-dimensional image of the subject's face so that the 3-D representation may be used in a beauty analysis and/or in a simulated use of one or more beauty products.

In another aspect, there is a computer readable medium containing instructions for a method.

In another aspect, there is a system including a processor configured to perform a method.

The preceding description is intended to provide the reader with a very abbreviated flavor for a few aspects of the invention and is not intended to limit the scope of the multifaceted invention described and claimed herein.

BRIEF DESCRIPTION OF THE DRAWINGS

The accompanying drawings, which are incorporated in and constitute a part of the specification, exemplify certain aspects of the invention and, together with the description, serve to explain some principles of the invention.

FIGS. 3A and 3B are exemplary before and after facial images, respectively, consistent with the present invention;

FIG. 7 is an exemplary user interface for use with the exemplary color calibration method, consistent with the present invention;

DESCRIPTION OF EXEMPLARY EMBODIMENTS

Reference is now made in detail to exemplary embodiments of the invention, examples of which are illustrated in the accompanying drawings. Wherever possible, the same reference numbers are used throughout the drawings to refer to the same or like parts.

One aspect of the invention may involve a method and system for enabling simulated use of an aesthetic feature on a simulated facial image. As explained in more detail below, the method and system may involve construction of a simulated facial image by using a facial construction program permitting selection of one or more facial features, for example.

Figure 1A:
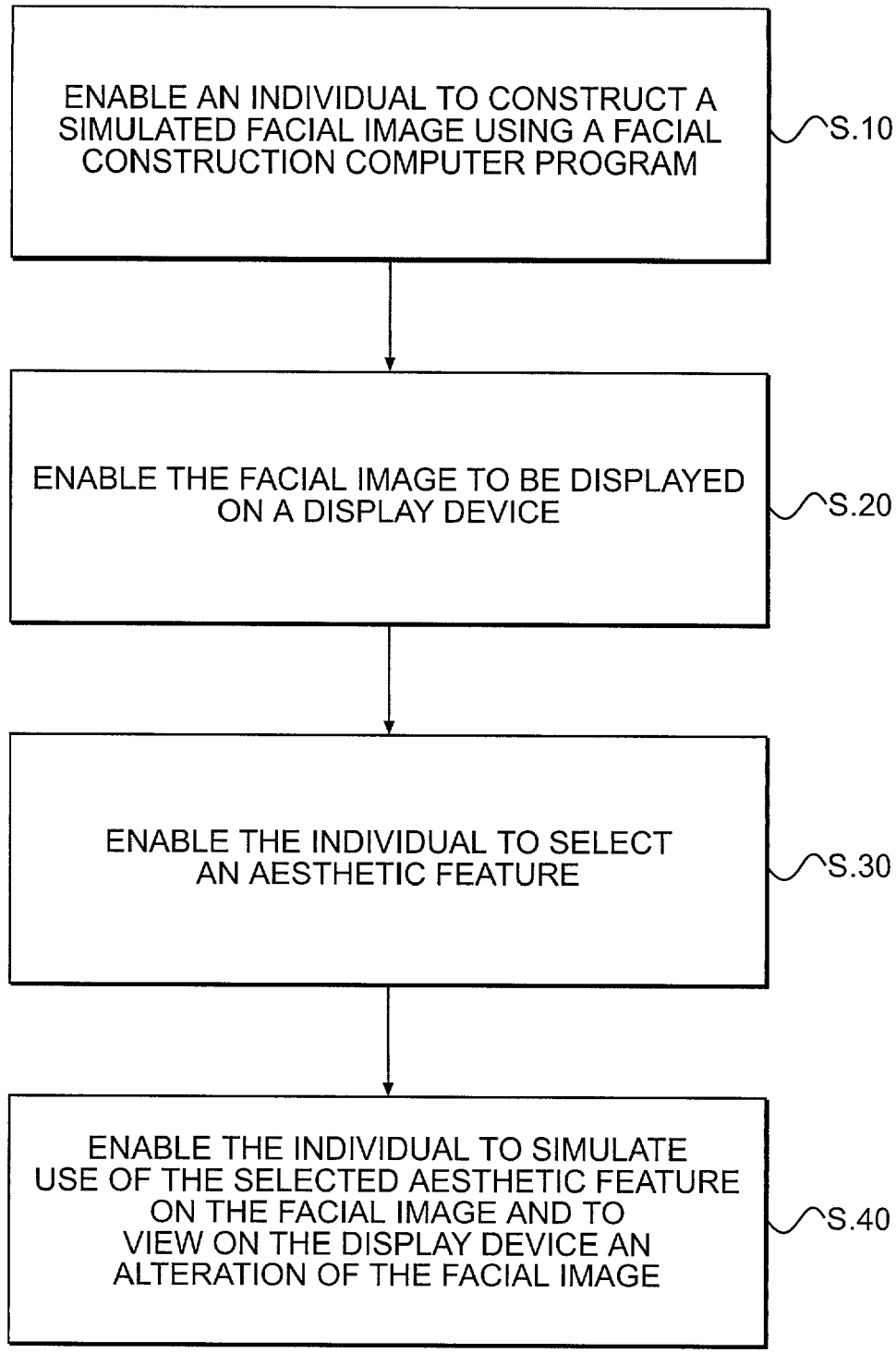
FIG. 1A depicts a flow chart of an exemplary method for enabling simulated use of an aesthetic feature on a simulated facial image consistent with the present invention.

FIG. 1A is a flowchart showing one example of a method according to the invention. As explained in more detail below, the method may involve enabling an individual to construct a simulated facial image using a facial construction computer program, where the facial construction computer program permits the individual to select at least one of a head, eyes, nose, lips, ears, and eyebrows (S.10); enabling the simulated facial image to be displayed on a display device (S.20); enabling the individual to select an aesthetic feature (S.30); and enabling the individual to simulate use of the selected aesthetic feature on the simulated facial image and to view on the display device an alteration of the simulated facial image having the simulated aesthetic feature (S.40).

As used herein the term "facial construction computer program" refers to any computer program that may be used to construct a facial image by selecting facial portions and/or facial features. This term includes programs, such as those used by police, other law enforcement agencies, intelligence related agencies, and security services, for constructing a facial image by selecting certain facial portions and/or features for the facial image simulation in a manner similar to the way a sketch artist makes a profile sketch of a suspect for them. Facial image construction computer programs include those referred to as crime-lab software, but they are not limited to such software.

Also, as used herein the term "aesthetic feature" refers to a beauty product, jewelry, eyeglasses, a body piercing (e.g., earrings, nose rings, and other forms of piercing), a tattoo, and/or another other type of item, substance, service, or action that might potentially alter a subject's facial appearance if a subject decides to implement it. The term "beauty product" refers to any product that may be used by an individual for a beauty reason. Examples of beauty products in the form of make-up include, but are not limited to mascaras, eye shadows, eye liners, foundations, concealers, blushers, lip liners, lip sticks, lip glosses, hair colorings, and any other substances that might be used to enhance a subject's outward appearance.

As indicated above, the method shown in FIG. 1A includes enabling an individual to construct a simulated facial image using a facial construction computer program, where the facial construction computer program permits the individual to select at least one of a head, eyes, nose, lips, ears, and eyebrows (S.10). The "enabling" of an individual to construct a simulated facial image may involve direct activity or indirect activity. For example, the "enabling" may involve providing access to the facial construction computer program via a network or through other channels such as a courier system. Examples of networks that may be used to receive the facial construction computer program include public networks, such as the Internet, telephony networks, private networks, virtual private networks, local area networks, metropolitan area networks, wide area networks, ad hoc networks, or any other mechanism for permitting communication between remote sites, regardless of whether the connection is wired or wireless. In a broader sense, a network includes a mechanism permitting communication between two or more nodes or remote locations. Examples of courier systems include the postal service or private couriers, such as United Parcel Service, Federal Express, etc. or any other mechanism for physically sending/receiving the facial construction computer program.

Physical transmission may involve causing a data storage device, which has the facial construction computer program stored on it, to be transferred to the individual. Examples of data storage devices that may be used to transfer the facial construction computer program include, but are not limited to, magnetic storage devices, such as floppy disks; optical storage devices, such as compact discs and digital video discs; organic storage devices; random access memories, such as DRAMs, SDRAMs, flash memories, and memory sticks, or any other mechanism capable of storing information.

Figure 2A:
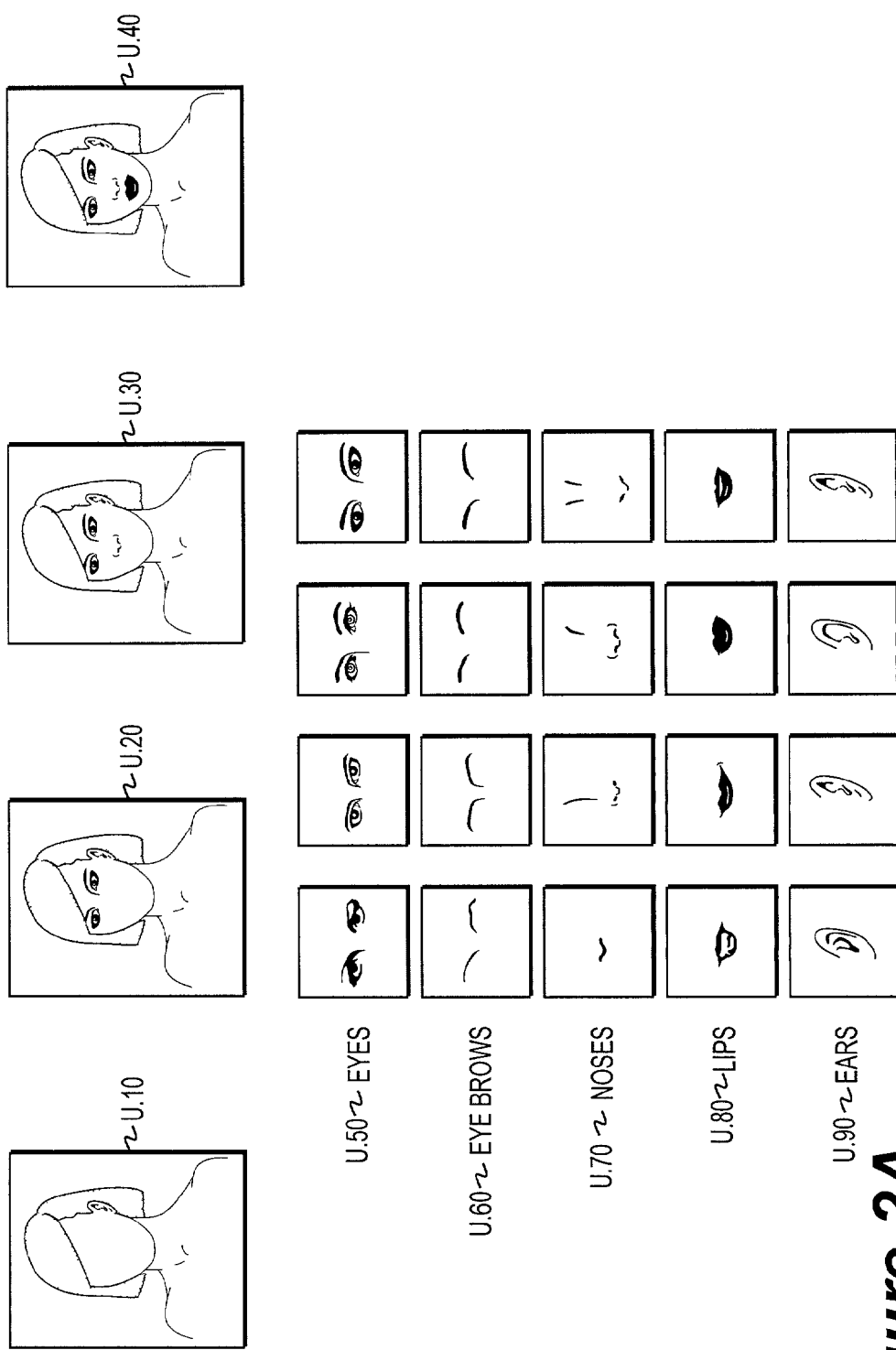
FIG. 2A is an exemplary user interface for a facial construction computer program consistent with the present invention.

Using the exemplary interface shown in FIG. 2, an individual may, for example: (1) select a head (e.g., blank facial) image (U.10), (2) select a pair of eyes, which may be displayed on the selected head (U.20), (3) select a nose, which may be displayed on the selected head (U.30), and (4) select a pair of lips, which may also be displayed on the selected head (U.40). To allow for the selections, the facial construction computer program may display on a display device, for example, a plurality of differing heads (not shown), a plurality of differing eyes (U.50), a plurality of differing eye brows (U.60), a plurality of differing noses (U.70), a plurality of differing lips (U.80), and a plurality of differing ears (U.90), and the program may permit the user to select a choice from each of the displayed pluralities of facial parts. As shown in the example of FIG. 2A, there could be a selectable template for each of the differing facial portions. A pointing device, such as a mouse, track ball, cursor control, joy stick, touch pad, or any other user controlled element could be used to select facial portion templates during facial image construction. Alternatively, any other known selection technique may be used.

As shown in the example of FIG. 2A, the program could be configured so that each facial portion is consecutively displayed on the facial image as it is selected. Alternatively (of in addition), the program may be configured so that the portions are displayed only after a plurality (or even all) of the selections have been made.

Although not shown in FIG. 3, the facial construction computer program may permit the individual to select other parameters such as the size and/or shape for the head, eyes, nose, lips, ears, and/or eye brows and/or the size and/or shape of at least part of the simulated facial image. The user might first select a generated category of facial image types, and then be presented with similar choices from which to select.

As mentioned above, and shown in FIG. 1A, the method may further include enabling the image to be displayed on a display device (S.20). Enabling the image to be displayed may be accomplished in one or more of a variety of direct and indirect ways, including directly displaying the image on a display device, providing access to software that facilitates display, providing network access which enables display of the image on a user-controlled device, providing a dedicated use device, or cooperating with an entity who either directly displays the image or who helps the user to display the image.

A method consistent with the invention may include (1) applying coloration to the simulated facial image, (2) selecting hair for the simulated facial image, and/or (3) selecting an eye color for the simulated facial image. Each of these actions may be accomplished by the individual using a user interface, similar to the one shown in FIG. 2, for example. Alternatively, as with the definition of "enabling display" above, the term "applying" and "selecting" as used throughout this application are also to be interpreted as including direct and indirect actions, such as, for example, providing access to software, providing access to a network site, cooperating with a third party who aids a user, or by participating in any way in activities that aid a user in applying and selecting.

Automatic or semiautomatic techniques known in the art can be used to add dimension and lighting effects to the simulated facial image. For example a virtual light source could be defined somewhere in the image, e.g., in the upper right hand corner of screen. Color could be applied homogenously, and then hue, tint, and shade may be modified based on the position of the virtual light source. Povray, a Unix based program, for example, adds dimensional aspects to a three-dimensional image to account for lighting. Using such techniques or any other known technique, the simulated facial image could be a three-dimensional image while the selectable facial portions are displayed in either two-dimensional or three-dimensional form. Alternatively, the simulated facial image could be a two-dimensional image and the selectable facial portions could be either 2-D or 3-D.

When the method involves templates of facial portions (e.g., lip, eyes, etc.), the templates may be segmented at the time of construction. Each template may be a morphological recreation that embodies the dimensional aspects of a facial portion such that relative dimensions of the facial portion are predefined and the color may be non-homogenous and changing with dimension.

Figure 2C:
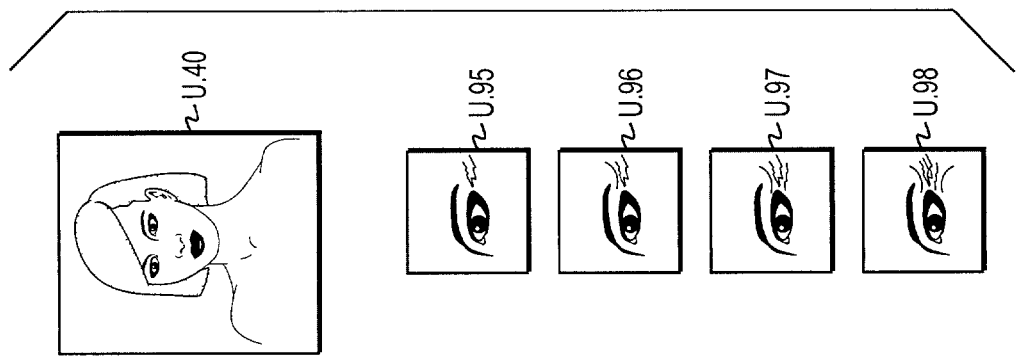
FIG. 2C is another example of a user interface enabling selection of an external body condition to be simulated on a facial image.
Figure 2B:
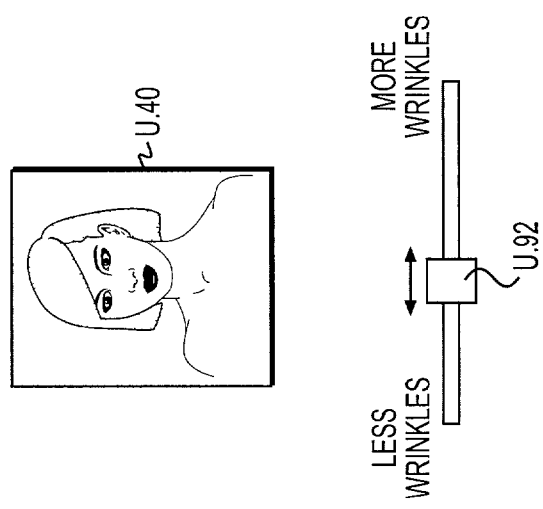
FIG. 2B is an exemplary user interface enabling selection of an external body condition to be simulated on a facial image.

The method may also involve enabling an individual to select at least one of a plurality of external body conditions and enabling simulation of the selected external body conditions on the simulated facial image. FIG. 2B shows an exemplary user interface having a movable control element U.92 capable of being moved to cause increasing or decreasing appearance of wrinkles or any other skin conditions, for example, in the simulated facial image U.40. FIG. 2C shows an exemplary user interface wherein templates in the form of representations of external body conditions (e.g., wrinkles U.95, U.96, U.97, U.98 of varying appearance) are capable of being selected to cause the external body condition of a selected template to appear on the simulated facial image U.40. When the simulated facial image U.40 is constructed using facial portion templates as shown in the example of FIG. 2A, one of more of the facial portion templates could be displayed along with an overlay of a body condition corresponding to a selected body condition template.

For example, an individual might first select a forehead template showing a particular shape of a forehead, and the individual might then select a template having wrinkles that may be overlayed on the forehead template. Having the subject select the template representing the external body condition may allow the simulated facial image to be constructed from the individual's perspective and, when the individual is simulating a facial image of himself/herself, it might provide a better indication of the actual condition of the individual's external body condition. Such information may be helpful when using the simulated facial image to conduct a beauty analysis, such as determining a beauty product to be recommended to the individual.

A database might contain each of the templates. Templates may exist for variety of differing external body conditions, such as skin conditions like wrinkles, skin color, homogeneity, skin tone, micro reliefs, or any other skin condition.

Additionally, the method illustrated in FIG. 1A may further include enabling the individual to apply coloration to the simulated facial image to simulate at least one of an actual skin tone and an actual hair color. As part of this step, a user interface may display a plurality of differing colors and permit the individual to select at least one choice from the plurality of displayed colors. As used throughout this document, enabling includes direct and indirect actions, as discussed herein.

Also, as mentioned above and shown in FIG. 1A, a method consistent with the invention may further include enabling the individual to select one or more aesthetic features (S.30). The individual may select an aesthetic feature using human-computer interaction techniques. Such techniques may include, but are not limited to, pull down menus, lists, buttons, scroll bars, using pointing devices, or any other user-interface elements. For example, enabling the individual to select an aesthetic feature may include enabling a plurality of representations of aesthetic features to be displayed on the display device and enabling the individual to select one of the displayed representations. This may occur directly or indirectly, as discussed earlier. Thus, providing the individual with access to software is within the definition of enabling selection of aesthetic features.

Further, enabling the individual to select an aesthetic feature may include enabling an individual to select a color for the aesthetic feature. Such a selection may be made, for example, using any of the user-interface elements mentioned above.

A method consistent with the invention may further include enabling the individual to simulate use of the selected aesthetic feature on the facial image and to view on the display device an alteration of the simulated facial image having the simulated aesthetic feature (S.40 in FIG. 1A). This may include simply presenting the aesthetic feature on the facial image using known image processing technique, such as holography, optical imaging, morphing, and/or other image processing mechanisms. An example of before and after processed images are presented in FIGS. 3A and 3B, respectively. As shown in FIG. 3A, the individual may begin with an initial simulated facial image (U.100), which may have been constructed using the facial construction computer program discussed above. Once the individual selects one or more aesthetic features such make-up (e.g., lipstick, eye shadow, etc.), the individual may simulate use of the aesthetic features on the facial image and view on the display device an alteration of the simulated facial image having the simulated aesthetic features (such as shown in U.110, FIG. 3B). The display of each aesthetic feature may occur substantially simultaneously with the selection of each feature or there could be a time delay.

Further, enabling the individual to simulate use of the selected aesthetic feature on the facial image may include permitting the individual to select a portion of the facial image to be altered with the simulated aesthetic feature An embodiment of the invention may include enabling storage of the simulated facial image and the altered facial image for selective recall by the individual. These images may be stored on any of the storage devices discussed herein.

The individual may be permitted to alter the simulated facial image based on a self-evaluation by the individual of the individual's own face. For example, in some instances construction of an initial facial image may involve defining the shape and location of major facial features, but may omit finer details such as skin tone and texture. Accordingly, the individual may be presented with at least one query prompting the individual to self-evaluate the individual's actual facial image. Thus, for example, the individual may be asked whether her skin is smooth or coarse. Such questions may be related to, but are not limited to, skin tone, skin color, hair color, eye color or any other visible characteristic of the individual. Reponses to such questions might cause automatic alteration of the simulated facial image. Alternatively, the user might be able to choose a feature to be applied to the image, such as discussed in association with FIGS. 2B and 2C. For example, the user might be provided with an array of skin tone choices, or may be able to choose an appropriate skin tone from a gradation bar.

When the aesthetic feature is a cosmetic product, simulating use of the selected cosmetic product may include simulating a process of the cosmetic product being applied on the simulated facial image. This may include, for example, simulated movement of a cosmetic product applicator so that the user may better understand how the cosmetic is to be applied. For example, FIG. 3b shows a cosmetic applicator product applicator being used to apply make-up. Such simulation may be accomplished using, for example, any known animation techniques, and may include simulation of any known applicators, such as mascara brushes, eye-liners, lipsticks, lip-glosses, lip-liners and any other physical device for use in applying cosmetic product to a subject.

The method associated with FIG. 1A might also include causing the simulated facial image to be displayed on a simulated likeness of at least a portion of a human. For example the simulated facial image may be displayed on a simulation of a full human body or on just the torso of a body. In another example, the method may include enabling selection of one or more articles of clothing and enabling the selected clothing article(s) to be displayed on the simulated human likeness. Alternatively (or additionally), the method might involve selection and display other items, such as jewelry or fashion accessories. Examples of some commercially available types of software for placing facial images on human likenesses and/or enabling selection of clothing include software products of My Virtual Model and Maya.

Figure 1B:
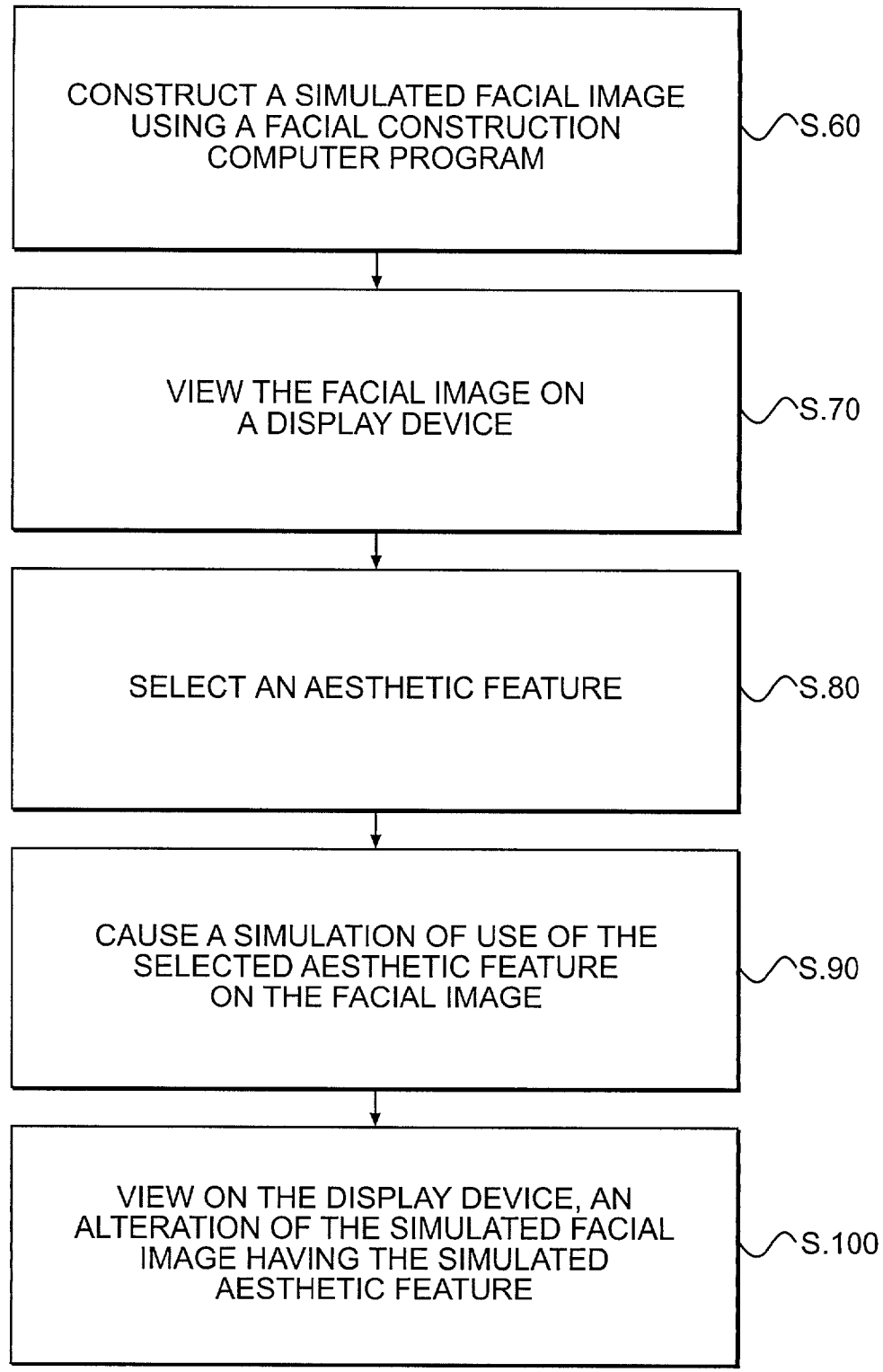
FIG. 1B is a flow chart of an exemplary method of simulating use of an aesthetic feature on a simulated facial image consistent with the present invention.

FIG. 1B is a flowchart of another exemplary method like the method of FIG. 1A, but from the user's perspective. The method may involve constructing a simulated facial image using a facial construction computer program, wherein constructing of the simulated facial image using the facial construction computer program comprises selecting at least one of a head, eyes, nose, lips, ears, and eye brows (S.60); viewing the image on a display device (S.70); selecting an aesthetic feature (S.80); causing a simulation of use of the selected aesthetic feature on the facial image (S.90); and viewing, on the display device, an alteration of the simulated facial image having the simulated aesthetic feature (S.100)

Since one of ordinary skill in the art will appreciate that the method of FIG. 1B corresponds to the method shown in FIG. 1A, further discussion is omitted. A similar correspondence exists between the methods shown in FIGS. 4A and 4B, explained below, the methods shown in FIGS. 6A and 6B, explained below, and the methods shown in FIGS. 10A and 10B, explained below.

Figure 4A:
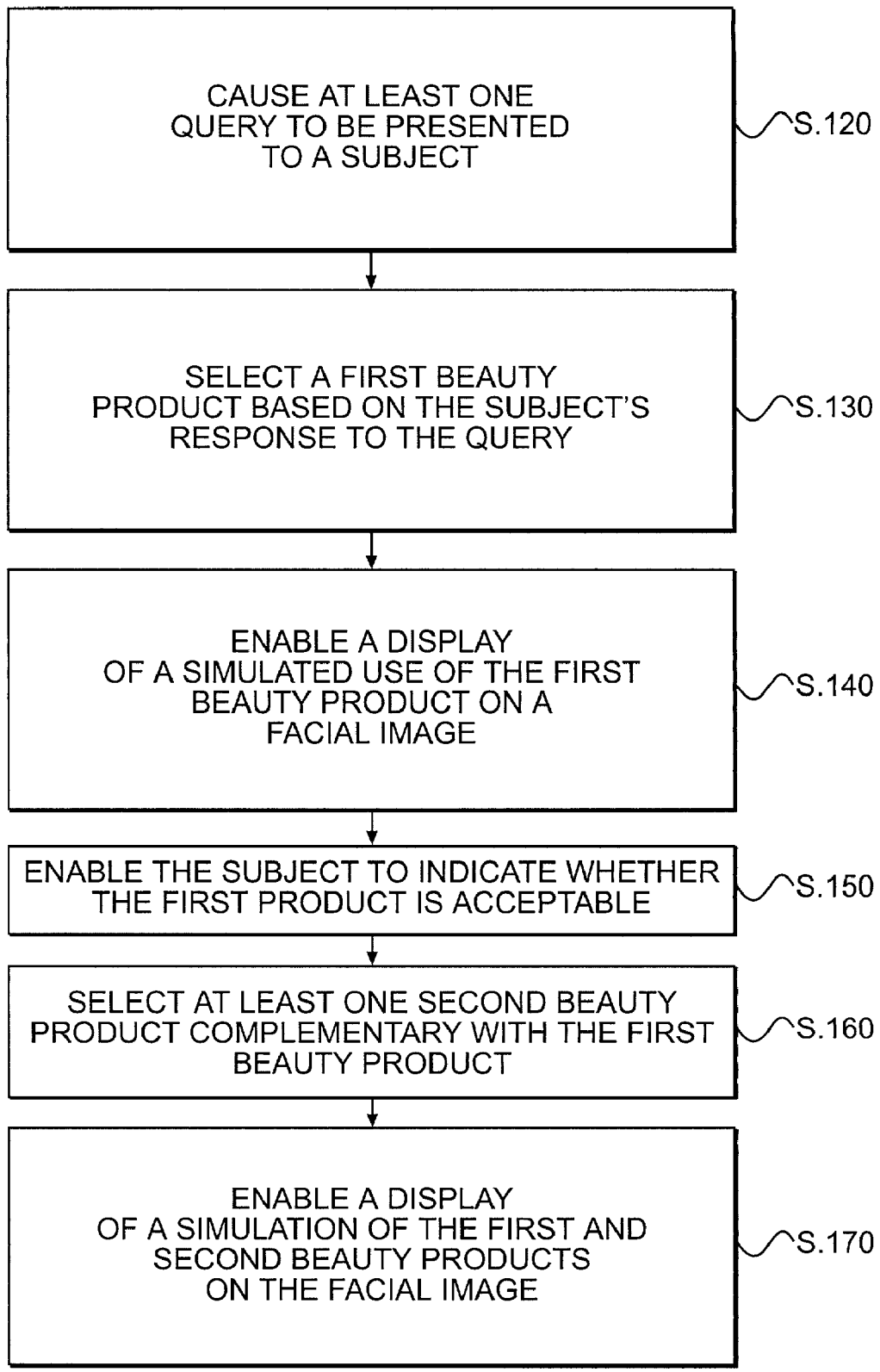
FIG. 4A is a flowchart of an exemplary method for recommending at least one complementary beauty product consistent with the present invention.

FIG. 4A is a flowchart of a method of recommending at least one complementary beauty product, consistent with an exemplary aspect of the invention. As explained in more detail below, such a method may involve causing at least one query to be presented to a subject (S.120); selecting a first beauty product based on the subject's response to the query (S.130); enabling a display, on a display device, of a simulation of the first beauty product applied on a representative facial image (S.140); and enabling the subject to indicate whether the first beauty product is acceptable (S.150). When the first product is indicated as being acceptable, the method may further include selecting at least one second beauty product complementary with the first beauty product (S.160); and enabling a display on the display device, of a simulation of the first and second beauty products applied on the facial image (S.170).

Figure 5:
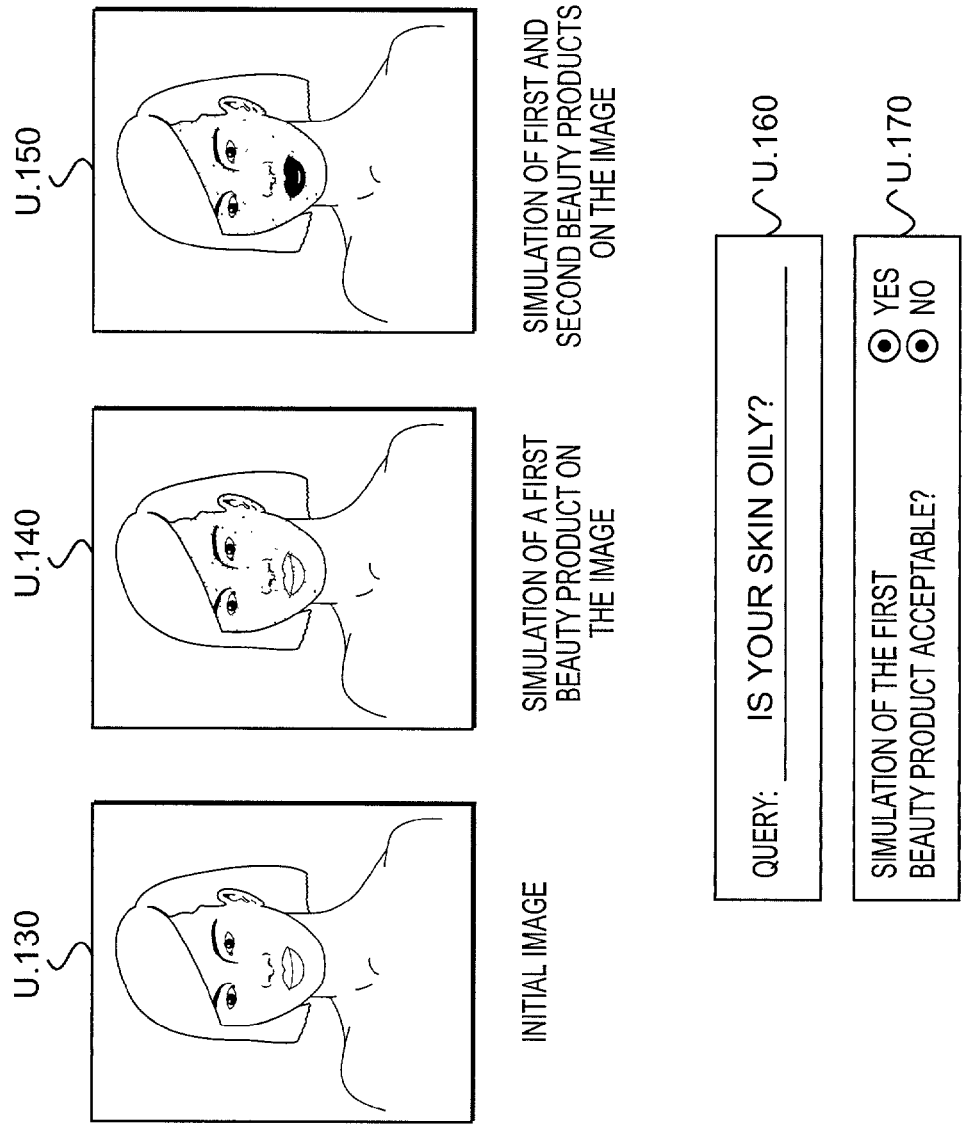
FIG. 5 is an exemplary user interface depicting simulated use of first and second beauty products on a facial image, consistent with the present invention.

As used herein the term "query" refers to a question or prompt in any form that may be presented to a subject to encourage a response from the subject. The query could be presented in any manner enabling the subject to perceive it. For example, the query could be presented in a visual form (e.g., text or image) or audio form. FIG. 5 shows a schematic example of a textual query U.160 associated with a user interface.

In one exemplary embodiment, the query may prompt the subject to input personal information such as physical attributes, lifestyle information, type of look, or personal preferences. Examples of lifestyles might include, but are not limited to: free spirited, adventurous, partier, alternative, and religious. Examples of looks include, but are not limited to, conservative, modern, hot, cool, chic, and retro.

As mentioned above, the method shown in FIG. 4A may include selecting a first beauty product based on the subject's response to the query (S.130). A first beauty product may be automatically selected by analyzing the subject's response using any analytic technique. Such analytic techniques may include, but are not limited to, statistical analysis, modeling, textual analysis, collaborative filtering, artificial intelligence and any other technique that may correlate selection of a first beauty product to a subject's response. Such correlations may be based on populative data or on the experience of experts. Examples of artificial intelligence engines include one or more of a neural network, a constraint program, fuzzy logic, classification, symbolic manipulation, fuzzy set theory, evolutionary computation, cybernetics, data mining, approximate reasoning, derivative-free optimization, and soft computing. Artificial intelligence techniques are disclosed in concurrently filed applications incorporated herein by reference.

Alternatively, in a method consistent with the invention, the first selected product may be selected from a type of the subject's choosing. For example, if the subject expresses interest in lip stick, analytic techniques may be used to identify a lip stick likely to be compatible with the subject.

The method shown in FIG. 4A may further include enabling a display, on a display device, of a simulation of the first beauty product applied on a representative facial image (S.140). Such simulation of the first beauty product may be accomplished in a manner similar to that discussed above with respect to step S.30 in FIG. 1A. Image U.140 in FIG. 5 shows an example of a simulation of a first beauty product (e.g., foundation) on a facial image.

Also, as discussed above, the method of FIG. 4A may further include enabling the subject to indicate whether the first beauty product is acceptable (S.150). For example, the subject, after viewing a simulation of the first beauty product might dislike the selection and choose to start over. If the subject wishes to proceed, she may indicate acceptance using, for example, a selectable interface area (U.170) shown in FIG. 5. The interface may include one or more of a displayed button, voice recognition response, or any other mechanism permitting user response. Thus, enabling the subject to indicate acceptance may include providing a selection mechanism to the subject so that the subject may make a selection. This may be accomplished by making accessible to the subject, software for the subject to access via a network or to load onto a personal computer.

If the user indicates that the first product is unacceptable, the method may further include selecting an alternative first beauty product and enabling a display, on the display device, of a simulation of the alternative first beauty product applied on the representative facial image. The alternative first beauty product may be selected using any of the analytic techniques discussed above. Also, the subject may indicate whether the alternative first beauty product is acceptable, as previously discussed.

Once a first product is deemed acceptable to the subject, the method of FIG. 4A may proceed to step S.160 where a second beauty product complementary to the first beauty product may be selected. As used herein, the term "a complementary product" includes one that is either physically, physiologically, biologically, or aesthetically compatible with the subject. Physical compatible may include for example, the fact that a product is unlikely to cause an adverse allergic reaction, and physically blends well with another product. Aesthetic compatibly refers to the fact that two products are aesthetically appealing (or do not clash) when worn together. Information elicited from experts and/or populational studies may be stored in a data structure and tapped to identify complementary products. The database may be searched in one of many ways described earlier, including, for example artificial intelligence algorithms.

Selecting the second beauty product may include identifying the second beauty product by using an artificial intelligence engine such as discussed earlier.

Image U.150 in FIG. 5 shows an example of a second beauty product (e.g., lipstick) displayed on a facial image along with a first beauty product (e.g., foundation).

In the method illustrated in FIG. 4A, the simulation of the first beauty product applied on the representative facial image (e.g., U.140 in FIG. 5) may be replaced on the display device by a new image U.150. Alternatively, as shown in the example of FIG. 5, images U.140 and U.150 may be simultaneously displayed.

Should the second beauty product be unacceptable to the subject, a method consistent with the invention, may include enabling the subject to so indicate and select at least one alternative second complementary beauty product in a manner similar to that described earlier in connection with the first alternative beauty product.

Once a subject is presented with one or more acceptable products, the subject may be provided with purchasing information. Such purchasing information may include, but is not limited to, pricing information, at least one location of a store selling the product, a link to a website selling the product, and/or information enabling a product purchase.

Figure 4B:
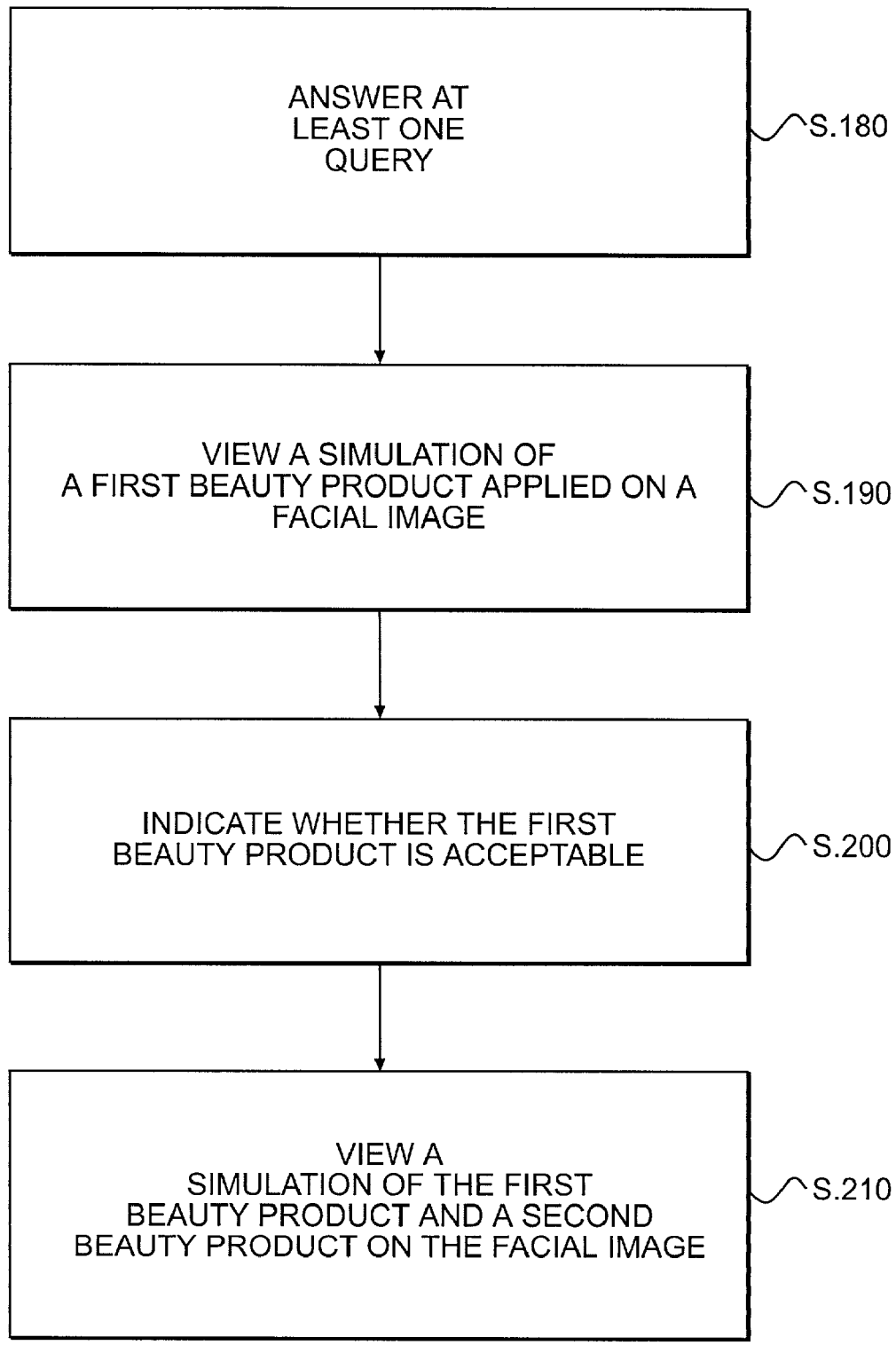
FIG. 4B is a flowchart of an exemplary method for receiving a recommendation for at least one complementary beauty product consistent with the present invention.

FIG. 4B is a flow chart of the method of FIG. 4A, from the subject's perspective. After answering at least one query (S.180), the subject may view on the display device, a simulation of a first beauty product selected based upon the subject's answer to the query (S.190). If the first beauty product is indicated acceptable (S.200), the subject may be presented with a complementary product displayed simultaneously on a facial image containing the first product. (S.210)

Figure 4C:
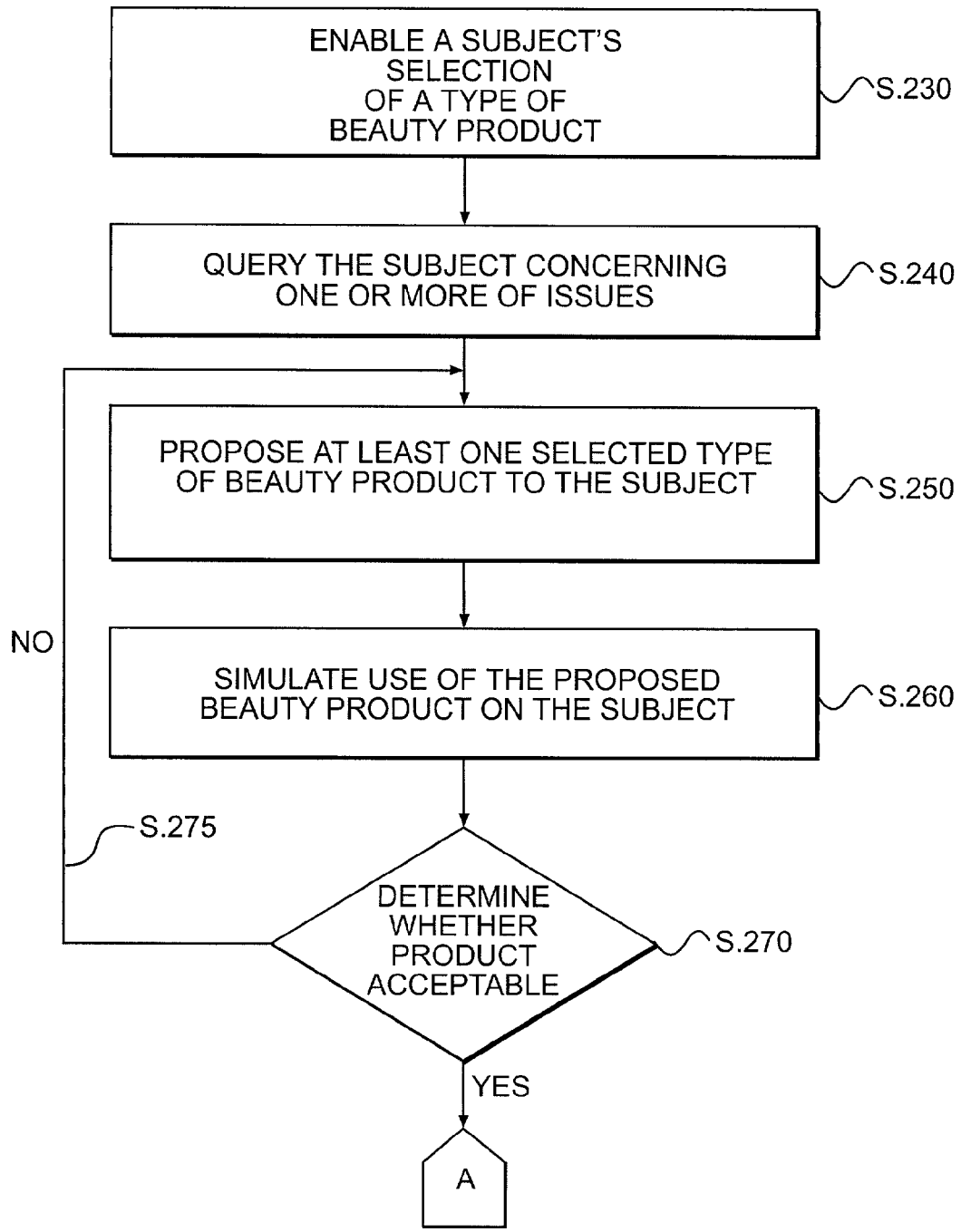
FIGS. 4C and 4D depict a two-page flowchart illustrating an exemplary method for receiving an order for at least one of the proposed products, consistent with the present invention.
Figure 4D:
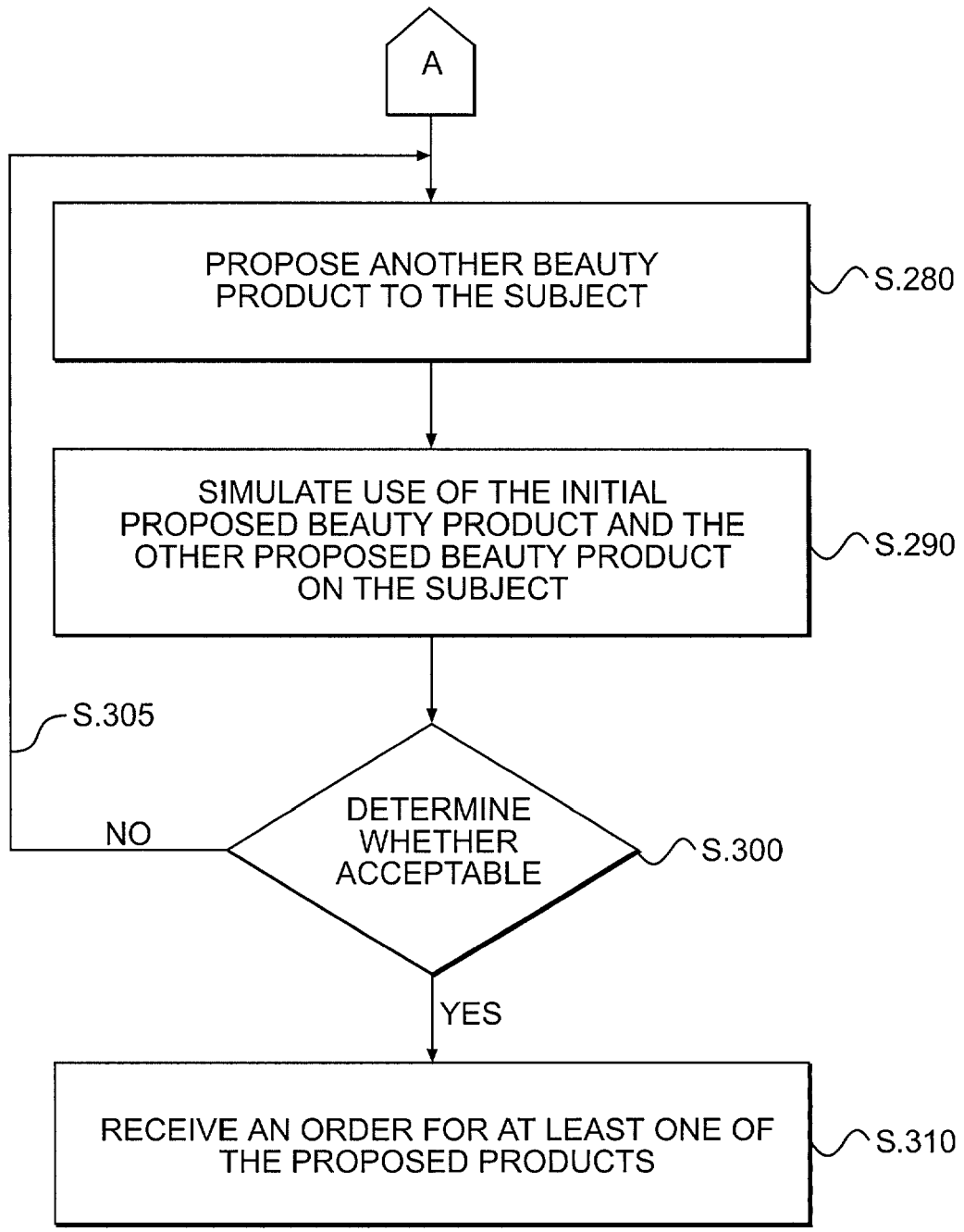

FIGS. 4C and 4D depict a two-page flowchart illustrating an exemplary method for receiving an order for at least one of the proposed products, according to the invention. The method may involve enabling a subject's selection of a type of beauty product (S.230); querying the subject concerning one or more issues (S.240); proposing at least one selected type of beauty product (S.250); simulating use of the proposed beauty product on the subject (S.260); determining whether the product is acceptable (S.270). If the product is acceptable, the method may include proposing another beauty product to the subject (S.280) simulating use of it on the facial image together with the first product (S.290) and if the subject wishes to order, receiving an order from the subject (S.300). If the subject expresses dissatisfaction with either the first selected product at step S.270 or the second proposed product at step S.300, the algorithm may loop (S.275 and S.305, respectively) allowing the subject to view an alternative proposal.

Figure 6A:
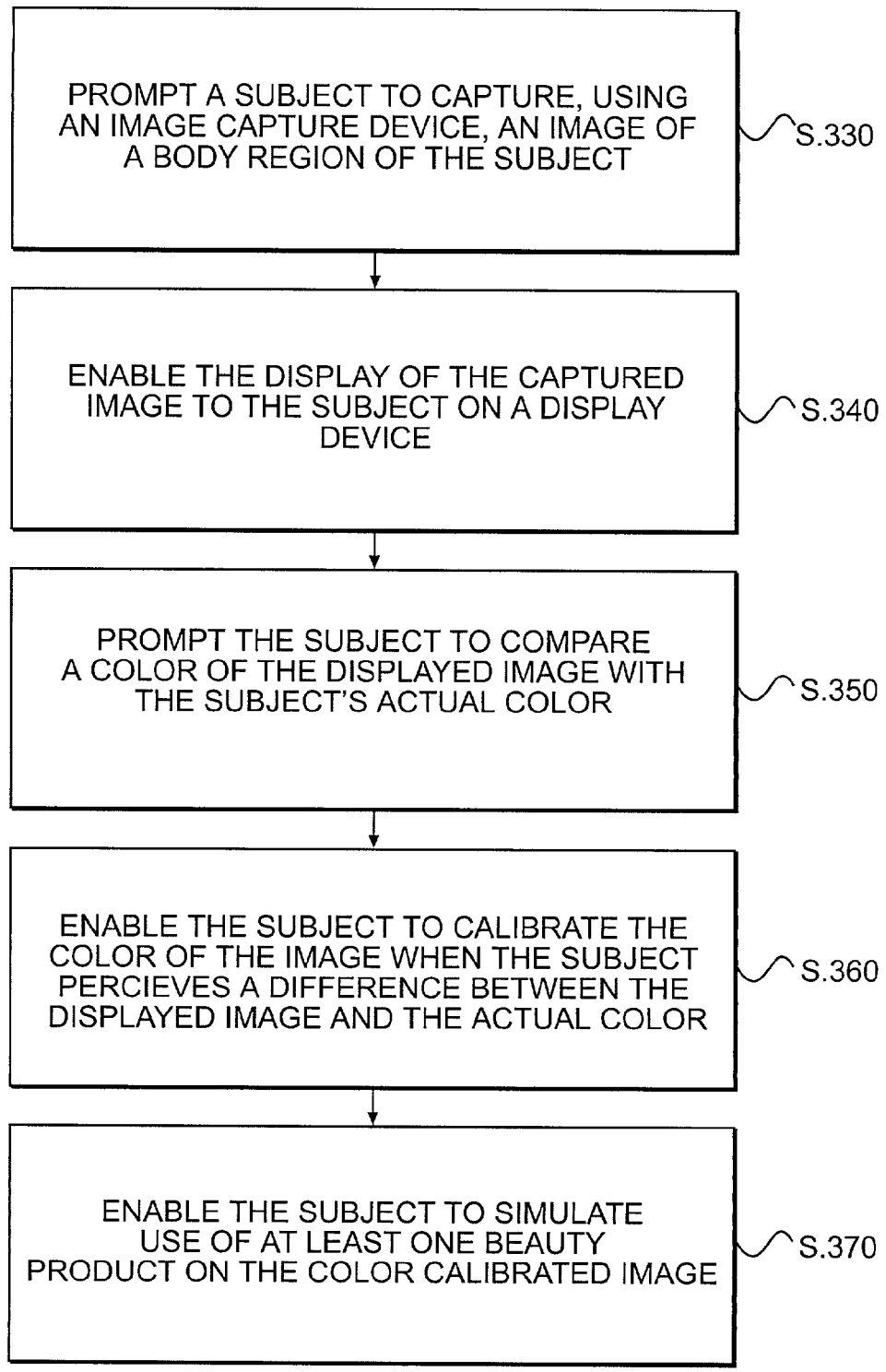
FIG. 6A is a flowchart of an exemplary calibration method consistent with the present invention.

FIG. 6A is a flow chart of an exemplary calibration method consistent with the invention. As explained in more detail below, the method may involve prompting a subject to capture, using an image capture device, an image of a body region of the subject (S.330); enabling the display of the captured image to the subject on a display device (S.340); prompting the subject to compare a color of the displayed image with the subject's actual color (S.350); enabling the subject to calibrate the color of the image when the subject perceives a difference between the displayed image and the actual color (S.360); and enabling the subject to simulate use of at least one beauty product on the color-calibrated image (S.370).

As used herein the term "color-calibrating" includes, but is not limited to, matching an actual color of the subject's skin with, for example, a color of the subject's skin that is displayed on a display device.

Prompting the user to capture a body region image (S.330) may be through a website or may occur by conveying a program to a machine accessed by the user. Prompting may also include one or more of providing instructions on how to go about capturing an image, providing a driver for an image capture device, providing image capture software, or providing access to a network site for facilitating image capture. Examples of image capture devices consistent with the invention may include, but are not limited to, web cams, digital cameras, analog cameras, scanners, and any other mechanism for capturing a visual representation of a body image.

The method of FIG. 6A may further include enabling the display of the capture image to the user on a display device (S.340). FIG. 7 shows an example of a captured image 180 being displayed on a display device 342. As used herein, the term "enabling display" is not limited to the direct act of displaying. It also includes indirect acts such as providing the user with access to software for causing the display to appear.

Once the image is displayed, the method may include prompting the subject to compare a color of the displayed image with the subject's actual color (S.350). For example, the subject may be prompted to compare the color of a displayed body region to the actual skin color of that body region. The subject may be prompted using text commands, voice commands, or through any other instructions eliciting a comparison.

FIG. 7 illustrates how a subject might compare the color of the displayed image 180 with the actual color of her hand 190 by placing her hand adjacent to the display device 342. The prompting of step S.350 may encourage the subject to make the comparison by providing the subject with directions or instructions to do so. For example, when the skin color (e.g., tone) on the subject's hand differs from the actual skin color of the body region, the subject may be prompted to make a more precise comparison (e.g., in FIG. 7, comparing the captured facial image with the subject's actual facial skin color rather than the skin color of the subject's hand).

Enabling the user to calibrate color may include enabling the display of a plurality of colors, enabling the subject to select one of the displayed colors closest to the actual color of the subject's body region, and enabling alteration of the displayed image to include the selected color. These actions may occur directly or indirectly. For example, the subject may be presented with a plurality of controls 40a, 40b, 40c, and 40d, each corresponding to a differing color, from which a particular color (e.g., 40c) may be selected (FIG. 7). The subject may be presented with a confirm button 240 to alter the displayed image to include the selected color, for example. As an alternative to exemplary displayed color controls 40c, 40c, 40c and 40d, a sliding continuum may be provided or the subject may be provided with some other control feature for making a positive color identification.

In a manner similar to that illustrated in FIG. 7, a subject may be enabled to select an actual hair color and/or an actual eye color.

Consistent with the invention, the user may be enabled to simulate use of at least one beauty product on the color-calibrated image (S.370). Such enabling may occur through the provision of the beauty product simulation control 260 (FIG. 7). Such control button may be presented to the subject, for example, after at least one beauty product is selected from a plurality of beauty products via a beauty product selection control 250. Beauty product selection may be driven by the user or may occur automatically or semi-automatically, such as by selecting a product complementary to some other information relating to the user and/or the user's activity. A list, for example, corresponding to the plurality of beauty products may be displayed, providing the subject with recommended and/or pre-selected options for simulation.

Figure 6B:
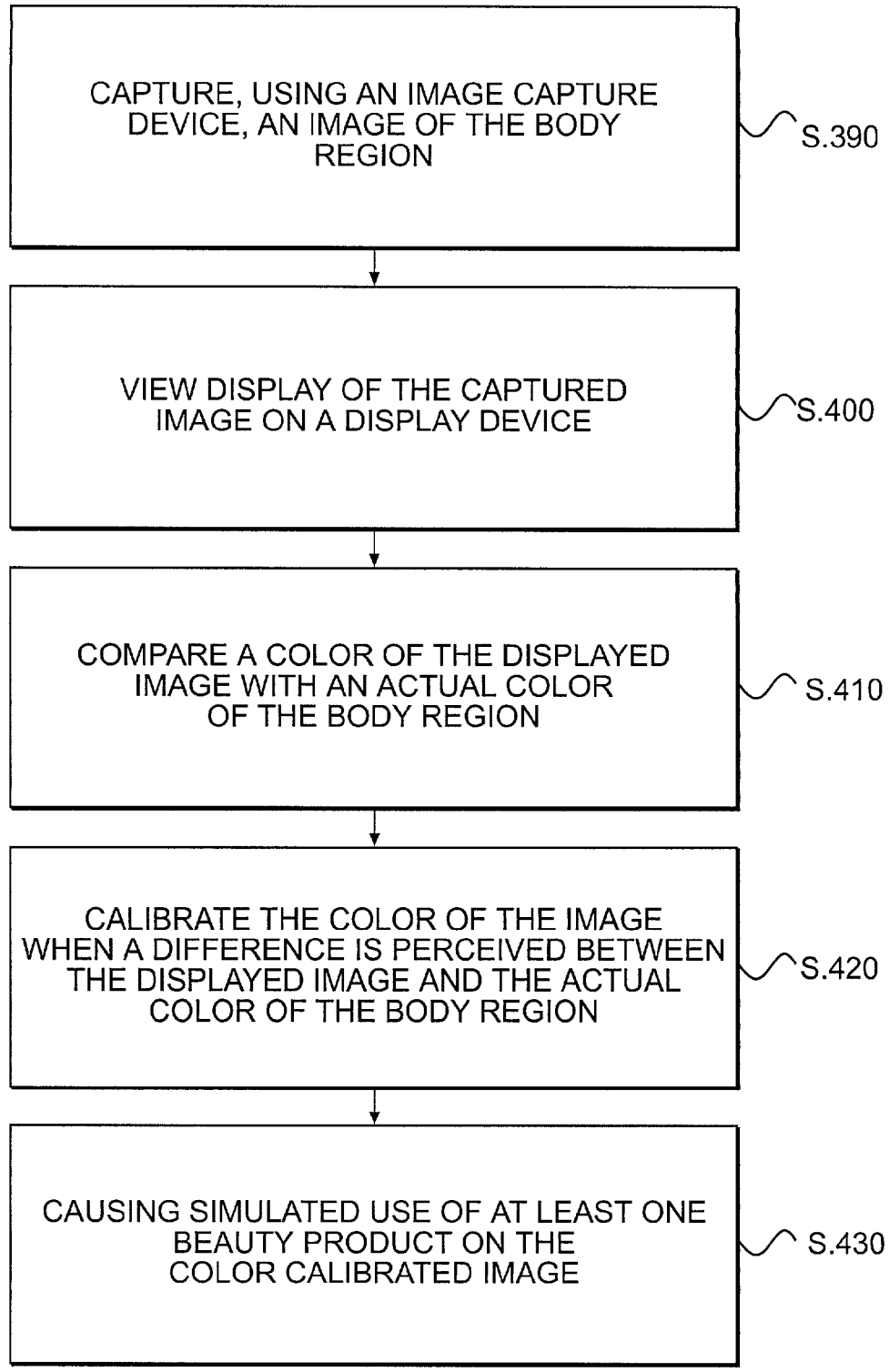
FIG. 6B is a flowchart of the exemplary calibration method from the user's perspective, consistent with the present invention.

FIG. 6B presents, from the user's perspective, a method like that of FIG. 6A. The method may involve capturing, using an image capture device, an image of the body region (S.390); viewing display of the captured image on a display device (S.400); comparing a color of the displayed image with an actual color of the body region (S.410); calibrating the color of the image when a difference is perceived between the displayed image and the actual color of the body region (S.420); and causing simulated use of at least one beauty product on the color-calibrated image (S.430).

Figure 8:
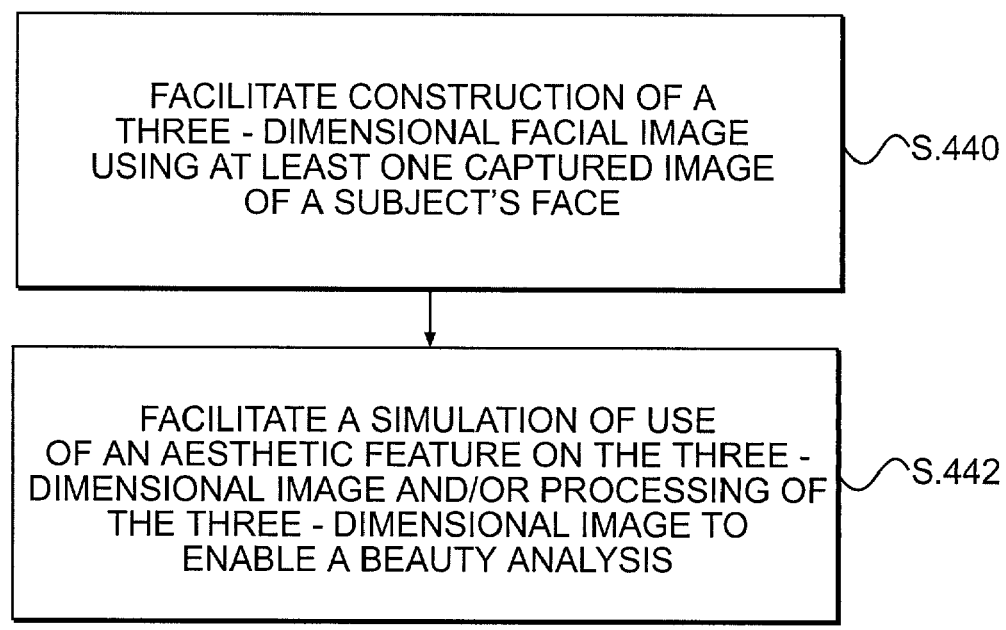
FIG. 8 is a flowchart of an exemplary method employing a three-dimensional image, consistent with the present invention.

FIG. 8 is a flowchart of an exemplary method of enabling an analysis using a three-dimensional facial image. As shown in this figure, the method may include facilitating construction of a three-dimensional facial image using at least one captured image of a subject's face (S.440). As explained in various portions of this document, the "facilitating" could involve either direct or indirect activity. For example, the phrase "facilitating construction" may include providing access to software for constructing the three-dimensional image based on at least one captured image of the subject. Access to the software may be provided through a web site or any other network location, such as where the software is maintained on a server. Software may be provided for storage on a machine in the custody and control of the user. For example, a memory storage device containing the software could be provided to the subject.

In yet another embodiment, a dedicated machine containing the software might be provided for the subject's use. For example, the dedicated machine might be located in a kiosk or may be a computer located in a sales establishment, such as a retail store or beauty facility.

Any known technique could be used to construct the three-dimensional image. For example, techniques for constructing three-dimensional images have been used in the movie industry to create movies, such as "The Matrix," "Toy Story," and "Final Fantasy". Some of these known techniques involve mapping actual actors.

The facilitating of construction of the three-dimensional image may involve facilitating the construction of the three-dimensional image using either a single captured image of subject or a plurality of such captured images. When a single captured 2-D image is used, the construction of the three-dimensional image may involve applying the captured image in a virtual manner on a three-dimensional frame to construct the three-dimensional image. Such a three-dimensional frame may be a frame stored in a database or it may be a generated frame, which is generated based on either stored data or input data. For example, the three-dimensional frame could be in the form of a virtual wire mesh.

The captured image(s) used to construct the three-dimensional facial image may be captured by the subject or captured by another individual, entity, or device. The captured image(s) may be an image(s) stored in a database or any form of data storage medium.

Figure 9B:
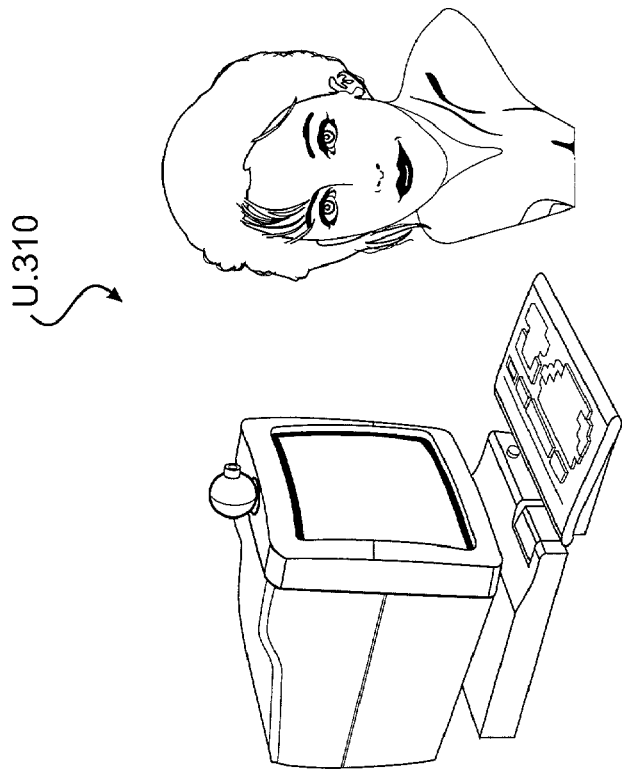
FIGS. 9A and 9B depict examples of capturing one or more images of the subject's face consistent with the present invention.
Figure 9A:
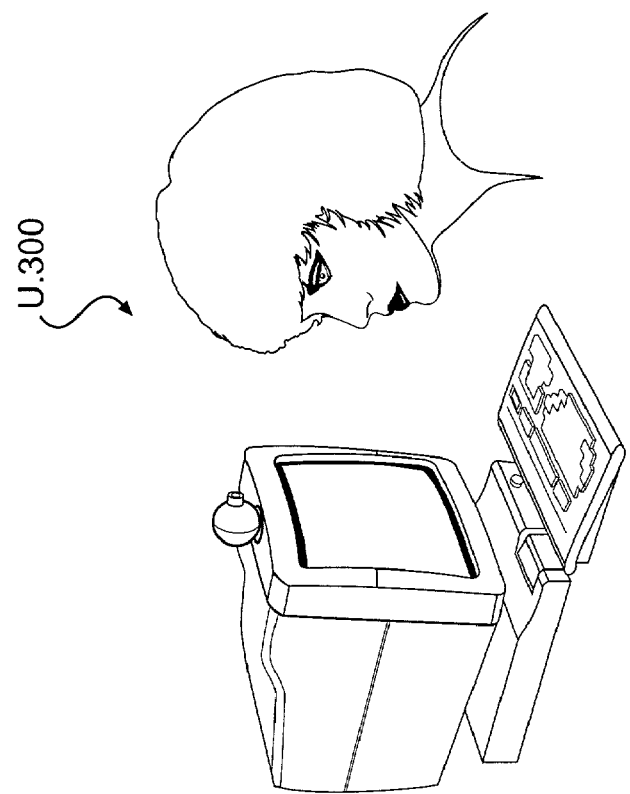

The method may include prompting a subject to capture one or more images of a subject's face. The prompting could take place in a manner like that discussed above in association with step S.330 of FIG. 6A, and the prompting may include instructions instructing the user about how to capture the image(s). The prompting may direct the subject to capture one or more facial images using a web cam, digital camera, analog camera, scanner, or any other image capture device. When multiple captured images are used to construct the three-dimensional image, the captured images may be images captured from differing perspectives, such as a substantially front view U.300 illustrated in FIG. 9A, and a substantially side view U.310 illustrated in FIG. 9B. In another example, the subject may rotate his/her head in front of an image capture device, and the image capture device may capture continuous motion or may snap a series of discrete images.

The method may also involve instructing the subject on how to transmit the captured image(s) to a location remote from a location of the subject, receiving the captured image(s) at the remote location, and/or constructing the three-dimensional image at the location. Any means of communication disclosed herein could be used to permit such transmission.

As illustrated in FIG. 8, the method may also include facilitating a simulation of use of an aesthetic feature on the three-dimensional facial image and/or processing of the three-dimensional facial image to enable a beauty analysis (S.442). In addition to the direct acts, "facilitating a simulation . . . and/or processing" may include an indirect act of providing a user with access to software in one of the various ways discussed previously. Such software may be software configured for performing the "simulation," the "processing," or a combination of both the "simulation" and the "processing."

Facilitating a "simulation of use of an aesthetic feature on the three-dimensional representation" may involve enabling the subject to simulate use of one or more aesthetic features (e.g., cosmetic products) on the three-dimensional facial image in a manner like that discussed above in association with the method of FIG. 1A and the examples shown in FIGS. 3A and 3B. The subject may be given the option of selecting the aesthetic feature from a plurality of differing aesthetic features. The aesthetic features could be any of the aesthetic features discussed previously in association with FIGS. 1A, 3A, and 3B. When the aesthetic feature is a beauty product, such as make-up, the use of the three-dimensional image may allow for more realistic viewing of the simulation of the aesthetic feature.

Simulation of use of an aesthetic feature on the three-dimensional facial representations may be accomplished using image processing techniques. In one exemplary embodiment, known image processing techniques could be used to "map" areas of the three-dimensional image where certain aesthetic features might be applied. For example, the location of lips in a three-dimensional area could be mapped to define an area where lip make-up might be simulated. Aesthetic features, such as beauty products, may be selected for simulation either directly by the user, or automatically as described above. In one example, the aesthetic features could be make-up products, such as mascaras, eye shadows, eye liners, foundations, concealers, blushes, lip make ups, hair coloring or any other product for enhancing aesthetic appearance of a subject.

The three-dimensional image may be revised to reflect projected changes in the subject's face as the result of use proposed beauty product. Any morphing technique may be used.

The method may also include enabling the three-dimensional image to be displayed on a human likeness and enabling selection of clothing, jewelry, or other item for the likeness, as discussed above in association with the method of FIG. 1A.

Consistent with an embodiment of the invention, a method may include enabling a subject to view the three-dimensional image from a plurality of differing virtual perspectives. A subject might be able to alter the virtual perspective from which the three-dimensional representation is viewed. This may occur by providing the subject with access to software for displaying a series of perspective images. Alternatively, the software might enable the subject to selectively toggle between various views. In yet another alternative, the user might be provided with one or more slider bars for selectively rotating the facial image in at least one of two planes.

By switching between perspectives, the user might obtain a better sense of how one or more aesthetic features may appear on her face. The method might also involve causing the subject to be presented with information enabling the subject to purchase one or more aesthetic features and/or receiving such a purchase order. For example, if the subject likes what he/she sees, he/she may be able to electronically purchase viewed aesthetic features over a network. That network may be the same network upon which the three-dimensional representation software resides.

Facilitating "processing of the three-dimensional facial image to enable a beauty analysis" may involve any one of a variety of differing activities. For example, the processing may involve identifying one or more external body conditions in the three-dimensional image and/or modifying the three-dimensional image to reflect evolution of the external body condition. A concurrently filed U.S. patent application entitled "Methods and Systems for Generating a Prognosis," Ser. No. 10/024,333, discloses examples of prognosis images reflecting evolution of an external body condition. In one exemplary embodiment, the facilitating of step S.442 may involve facilitating display of a time-lapsed simulation of the three-dimensional facial image.

In one example, when the captured facial images used in the construction of the 3-D image contains an external condition, the facilitating of step S.442 may involve analyzing the external body condition via the three-dimensional image. Such analyzing may occur at a location remote from a location of the subject. For example, a remote consultant, armed with the three-dimensional image, may be better skilled at analyzing the external condition. The analyzing might involve changing the perspective of the three-dimensional image as discussed above. In addition, the method may also include proposing a beauty product to the subject (e.g., transmitting a beauty product recommendation via any communication means disclosed herein), wherein the proposing may be based at least partially on the analyzing of the external body condition.

In another example, the facilitating of step S.442 may involve providing the subject with access to software configured to analyze an external body condition. For example, the software could use image processing techniques, such as those that may be capable of identifying the extent and severity of external body conditions. The software may be configured to propose a beauty product to the subject. Logic algorithms, such as those discussed previously, may identify an appropriate beauty product for use in addressing the external condition.

Computer graphics techniques may be used to generate a multi-dimensional image and/or simulate the subject's external body condition. Such techniques may also be used to model the evolution of the external body condition over time. For example, a three dimensional or a two dimensional image of a human face may be defined by its edges or points. Next, those points may be linked together by lines to create a wireframe rendering of the object representing the human face. In an exemplary embodiment, an MPEG-4 facial mesh characterized by Facial Definition Parameters (FDPs) may be used. Next, a two-dimensional image of the subject may be applied at the surface of the wire-frame. In some cases objects may be lit by a light source and may be shaded. Surfaces may be represented as polygons, or as B-spline patches, or by any other computer graphics technique. Any graphics application, such as OpenGL, Renderman, or VRML may be used for modeling an external body condition on a human anatomy.

A human face could be modeled with B-spline patches representing muscle patches on a representation of the human face. As part of representing facial muscles as B-spline patches, the nature and direction of muscle fibers may be taken into account. In general, the facial muscles are of two types: linear muscles and sphincter muscles. A linear muscle contracts toward an attachment on the bone such as the frontalis major muscle that raises the eyebrows. A sphincter muscle on the other hand, contacts around an imaginary central point such as the orbicularis oris muscle that draws them out together. In one exemplary embodiment, open B-spline patches may be used to simulate the linear muscles while closed B-spline may be used to simulate the sphincter muscles.

A human face may be modeled by noting that it is a layered structure composed of a skull, a muscle layer, an outer skin layer, and connecting tissue between the muscle layer and the outer skin layer. Tissue connecting the outer skin to muscles may be simulated with imaginary springs. Such a model is discussed in "A Plastic-Visco-Elastic Model for Wrinkles in Facial Animation and Skin Aging," by Wu et al., which is incorporated by reference in its entirety herein. Using this facial model in one exemplary embodiment, deformations associated with movements of face may be represented. Not only the elastic aspect of facial movement but also the plasticity of skin, which may develop with aging resulting in wrinkles, may also be incorporated as part of this facial model.

Using a modified version of the afore-mentioned model, in one exemplary embodiment, external body conditions, such as wrinkles may be simulated. An addition of a wrinkle may be used as an input to an existing mathematical model of the facial image, and the facial image may be modified accordingly. For example, a plasticity weighting factor associated with the part of the facial image where the wrinkle is to be added may be changed to cause simulation of the addition of the wrinkle. In one example, the mathematical model of the image may be modified when the subject submits a response to the self-evaluation prompt. In another example, a user may select a beauty product (for example, a wrinkle remover), and the mathematical model associated with the image may be modified to take into account the effect of the selected beauty product.

Other models and/or mathematical techniques may be used to simulate the user's self-evaluation and/or affects of beauty products. Optionally, these models and techniques may be used to simulate the affects of aging. In one example, rather than physically-based models, geometric models may be used to simulate an external body condition.

Figure 10A:
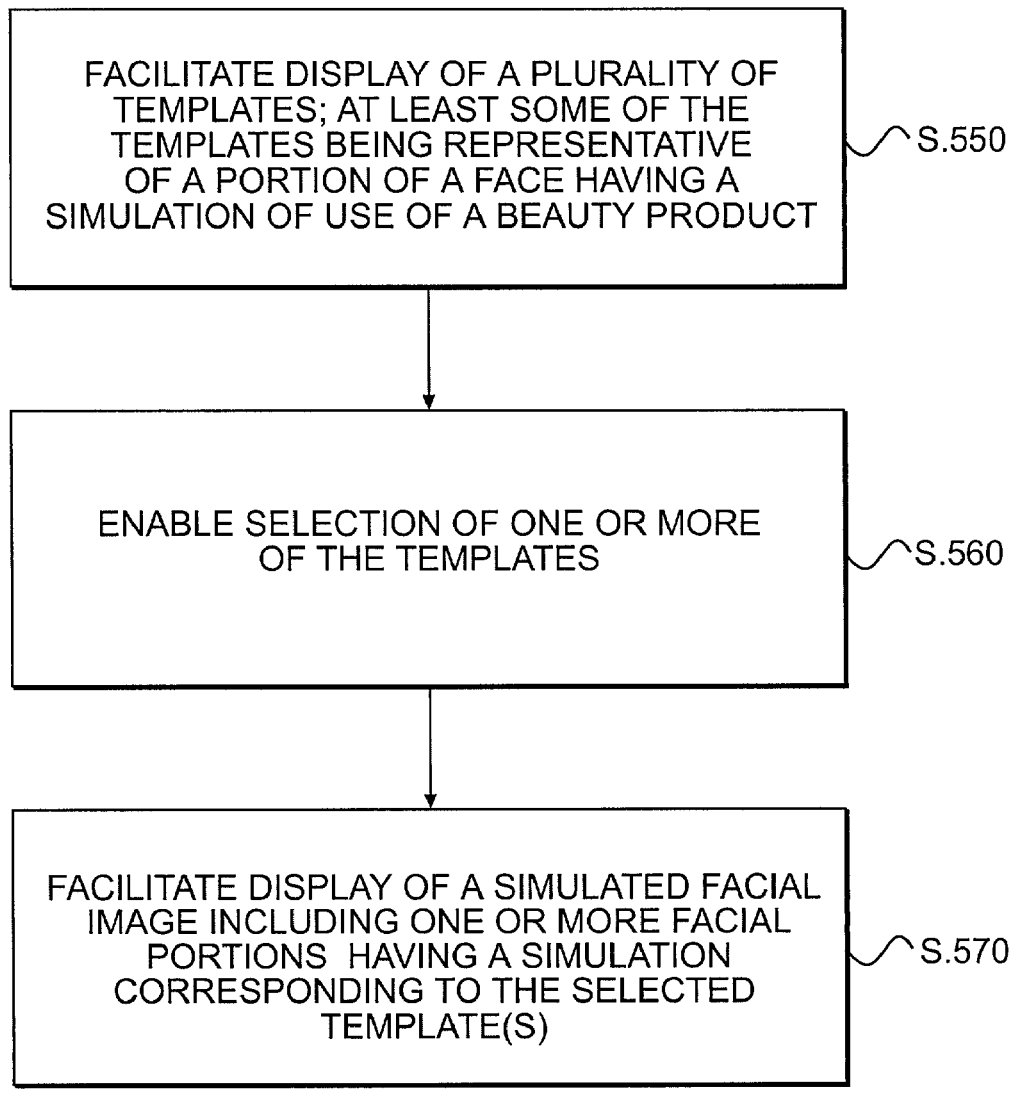
FIG. 10A is a flowchart of an exemplary method for enabling a beauty analysis consistent with the present invention.

FIG. 10A shows a flow chart of an example of a method of enabling a beauty analysis. The method includes facilitating display, on a display device, of a plurality of templates, wherein at least some of the templates are representative of a portion of a face having a simulation of use of a beauty product (S.550); enabling selection of at least one of the displayed templates (S.560); and facilitating display, on the display device, of a simulated facial image including at least one displayed facial portion having a simulation of use of a beauty product, wherein the displayed facial portion having a simulation corresponds to the at least one selected template (S.570). At least some of the templates in this example may be configured so that they are representative of one or more body portions having a simulation of a use of a beauty product. For example, when the beauty product is make-up, at least some of the templates may be configured so that they are representative of one or more body portions having make-up already applied thereto.

As mentioned above, the method includes facilitating display of a plurality of template (S.550). The facilitating of display could involve direct activity (e.g., displaying the templates) or indirect activity, such as providing access to software or any other form of indirect activity including the other forms discussed herein.

Figure 10B:
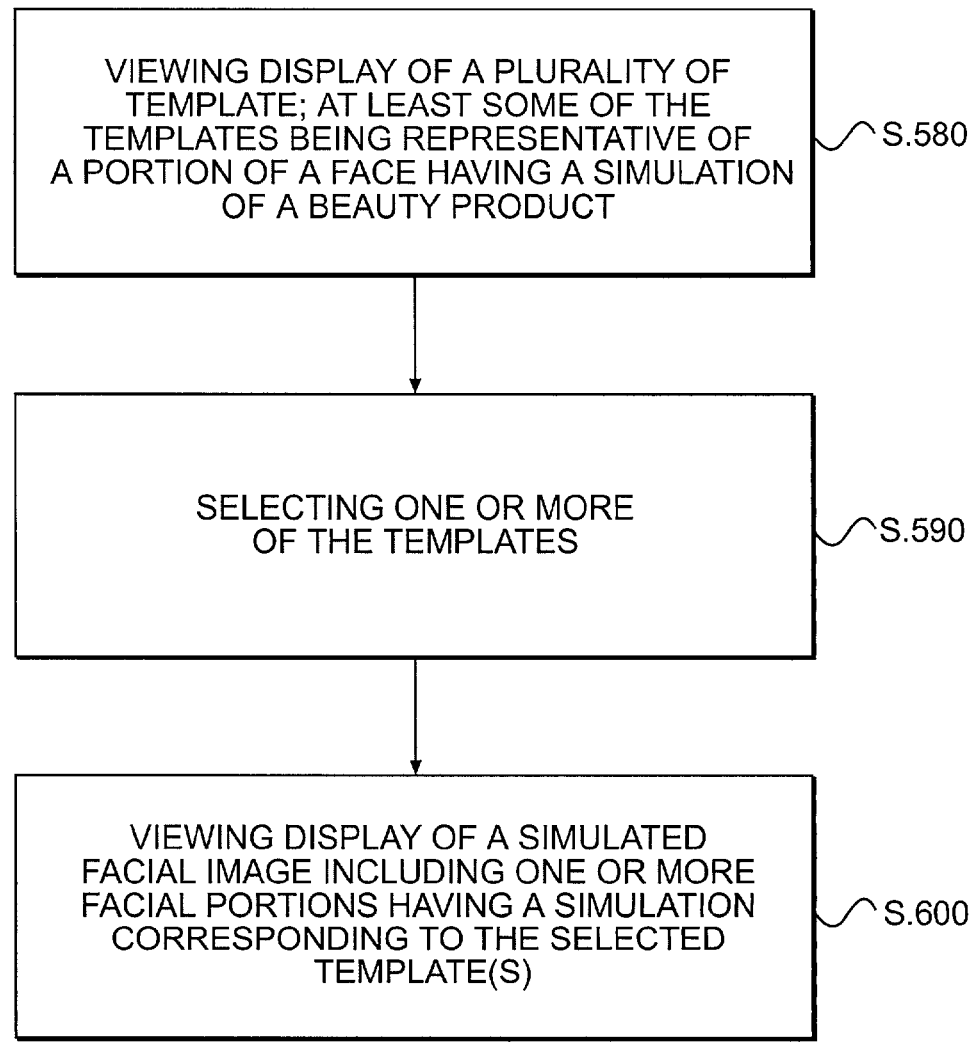
FIG. 10B is a flowchart of an exemplary method for enabling a beauty analysis consistent with the present invention.
Figure 10C:
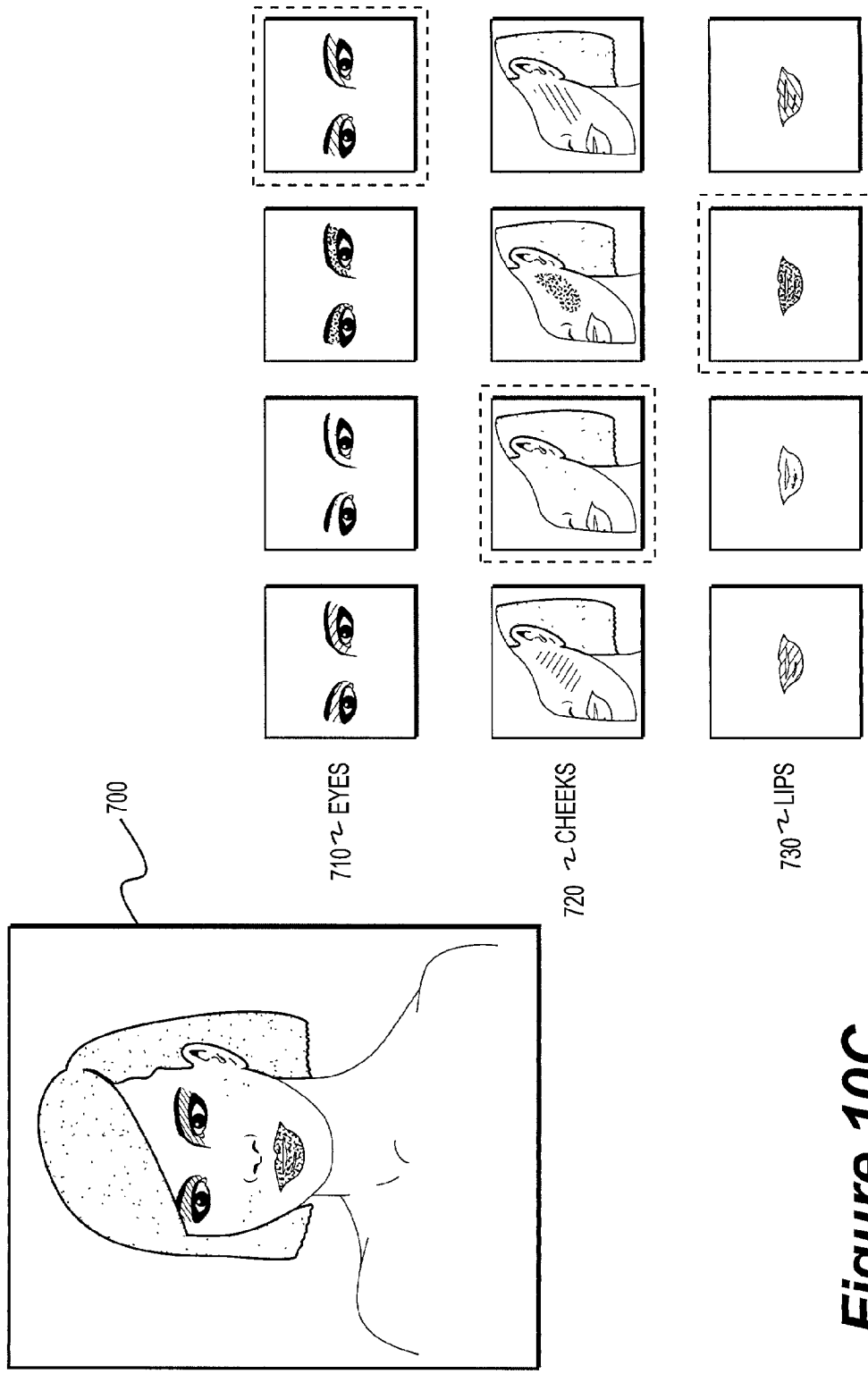
FIG. 10C is an exemplary user interface depicting selectable templates representative of a portion of a face having a simulation of use of a beauty product.

FIG. 10C shows an example of templates having a simulation of use of differing beauty products. The templates shown in example of FIG. 10C include a group of eye templates 710, wherein each of the eye templates 710 includes a simulation of using differing eye shadow make-up; a group of cheek templates 720, wherein each of the cheek templates 720 includes a simulation of using differing blush make-up; and lip templates 730, wherein each of the lip templates 730 includes a simulation of use of a differing lip make-up product, such as lip stick, lip gloss, or lip liner, for example. Each template in the respective group may have a simulation of a make-up product having a differing color, a differing texture, a differing brand, a differing formulation, and/or any other difference from the other templates in the respective group. For example, the first of the eye templates 710 may have a simulation of eye shadow makeup having a color, texture, brand, and/or formulation differing from that of the eye shadow products simulated in the other eye templates. The make-up could be a cosmetic product chosen from mascaras, eye shadows, eye liners, foundations, concealers, blushers, lip makeups, lip sticks, lip glosses, and hair colorings.

Although the example of FIG. 10C relates to differing make-up simulations, it should be understood that the exemplary method illustrated in the flow chart of FIG. 10A might involve differing simulations of other types of beauty products.

As shown in the example of FIG. 10C, the templates may include a group of templates (e.g., the group of templates 710, the group of templates 720, and the group of templates 730), wherein each template in the group has substantially the same shaped facial portion along with a simulation of a differing beauty product.

In one example of the method, at least some of the plurality of templates may include a group of templates each having a facial portion with a differing shape. Such an example might incorporate some of the features of the method discussed above in association with FIGS. 1A and 2A-2C. Optionally, the method associated with FIG. 10A might use a template configuration similar to that shown in FIG. 2A, wherein at least some of the templates are representative of lips, eyes, cheek, eyebrows, noses, ears, and/or other facial portions having differing shapes and/or sizes.

The method may also involve maintaining, accessing, and/or providing access to a database storing the templates.

As illustrated in FIG. 10A, the method further includes enabling selection of at least one of the displayed templates (S.560). The enabling could take place via any direct or indirect activity discussed herein. For example, the enabling might involve providing access to software having a selection feature. One or more of the templates could be selected in any known fashion. For example, the selection techniques discussed in association with the method of FIG. 2A and/or any of the other methods discussed herein could be used.

In another example, the method of FIG. 10A may include enabling an individual to select one of a plurality of differing external body conditions and enabling simulation of the selected external body conditions on the simulated facial image. For example, such enabling could take place in a manner similar to that discussed in association with the method of FIG. 1A, such as by enabling use of a user interface like that of FIG. 2B and/or FIG. 2C.

As discussed above, the method of FIG. 10A also includes facilitating display, on the display device, of a simulated facial image including at least one displayed facial portion having a simulation of use of a beauty product, wherein the displayed facial portion having a simulation corresponds to the at least one selected template (S.570). As with the facilitating of S.550, the facilitating of S.570 may involve any direct or indirect activity, such as providing access to software for causing the display.

The "displaying of a simulated facial image . . . " of S.570 of FIG. 10A might take place in a manner like that discussed above in association with S.40 of FIG. 1A. In one example of the method of FIG. 10C, as each template in one of the template groups 710, 720, and 730 is selected, a displayed facial image 700 may be altered to include a facial portion and a beauty product simulation corresponding to that of the selected template.

The templates and/or the simulated facial image may be either two-dimensional or three-dimensional. For example, two-dimensional templates may be used to form a three-dimensional simulated facial image.

Similar to the method discussed in association with FIG. 1A, the simulated facial image of the method of FIG. 10A could be displayed on a simulated likeliness of at least a portion of a human. In addition, the method may involve enabling selection of at least one article of clothing, jewelry, and/or any other item, wherein the selected item is displayed on the simulated likeness.

The method may further include enabling application of coloration to the simulated facial image to simulate at least one of actual skin tone and actual hair color. The method may also include enabling storage of the simulated facial image for selective recall by an individual.

FIG. 10B shows a method like that of FIG. 10A from a user-side perspective. The method of FIG. 10B includes viewing display, on a display device, of a plurality of templates, wherein at least some of the templates are representative of a portion of a face having a simulation of use of a beauty product (s.580); selecting of at least one of the displayed templates (S.590); and viewing display, on the display device, of a simulated facial image including at least one displayed facial portion having a simulation of use of a beauty product, wherein the displayed facial portion having a simulation corresponds to the at least one selected template (S.600).

Instructions corresponding to one or more of the methods described herein may be contained in a computer-readable medium. Computer-readable media could include any media discussed herein, including but not limited to, data storage devices like hard disks, floppy disks, and CD-ROM; a carrier wave received from a network like the Internet; and/or any forms of ROM or RAM.

One exemplary embodiment of the invention includes a system having a processor configured to perform one or more of the methods described herein. As used herein, the "processor" intended to include any possible structural arrangement configured to perform one or more of the methods and it is not limited to data processors or other forms of computer-based processors.

Figure 11:
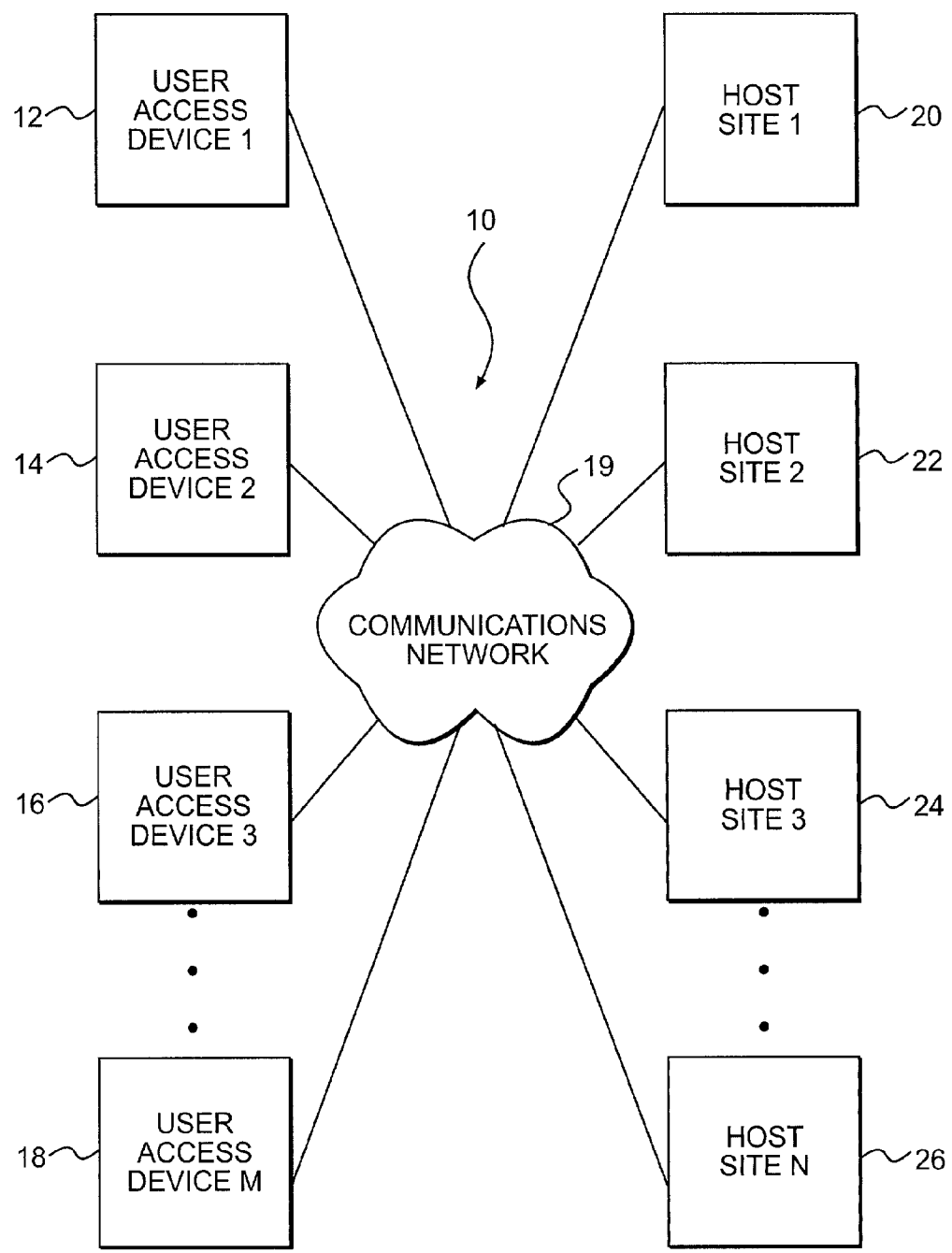
FIG. 11 is a diagram of an exemplary environment in which the systems and method consistent with the present invention may be implemented.

By way of a non-limiting example, FIG. 11 illustrates a system environment 10 in which at least some features and principles of the present invention may be implemented. As illustrated in the schematic diagram of FIG. 11, system environment 10 includes user access devices (1-M) 12-18 connected via a communications network 19 to host sites (1-N) 20-26. Using at least one of the user access devices 12-18, a user such as a consumer may connect to at least one of the host sites 20-26 through the communications network 19. A user access device consistent with the present invention may be based on any computing platform. Such user access devices include, but are not limited to, personal computers, internet access terminals, such as thin client devices, hand-held devices, such as palm pilots, or any other device with a computing module. A user access device may be located in one or more various places, including homes, stores, malls, airports, train stations, bus stations or any other location from which a user may connect to communications network 19 using a wired or a wireless connection.

A host site device consistent with the present invention may be a computing server or an information processing engine located anywhere. The host site device may be connected to at least one user access device via communications network 19.

Communications network 19 may comprise, alone or in any suitable combination, a telephony-based network (such as a PBX or POTS), a local area network (LAN), a wide area network (WAN), a dedicated Intranet, and/or the Internet. Furthermore, any suitable combination of wired and/or wireless components and systems may be incorporated into communications network 19.

Although FIG. 11 depicts each user access device connected to communications network 19, it need not be so. Instead of exchanging information with the host site using the communications network, a user may simply exchange the information using a removable storage device (item 42 shown in FIG. 12), such as an omega zip drive, or a memory stick device. Similarly, the host site need not be connected to communications network 19, but instead may exchange information with a user access device through a removable storage device. Information, such as simulated facial images, recommendations for a beauty product, color-calibrated images, or three-dimensional images could be supplied, conveyed, transmitted, and received in any known manner including any form of electronic communication, such as an e-mail message, a website on an electronic network, and/or a facsimile transmission. The information could also be sent via any non-electronic communication means, such as conventional postal delivery. It should be understood that while multiple user node devices and hosts are illustrated in FIG. 11, in a broader sense, a single host (and even a single user device) may be encompassed by the invention.

Figure 12:
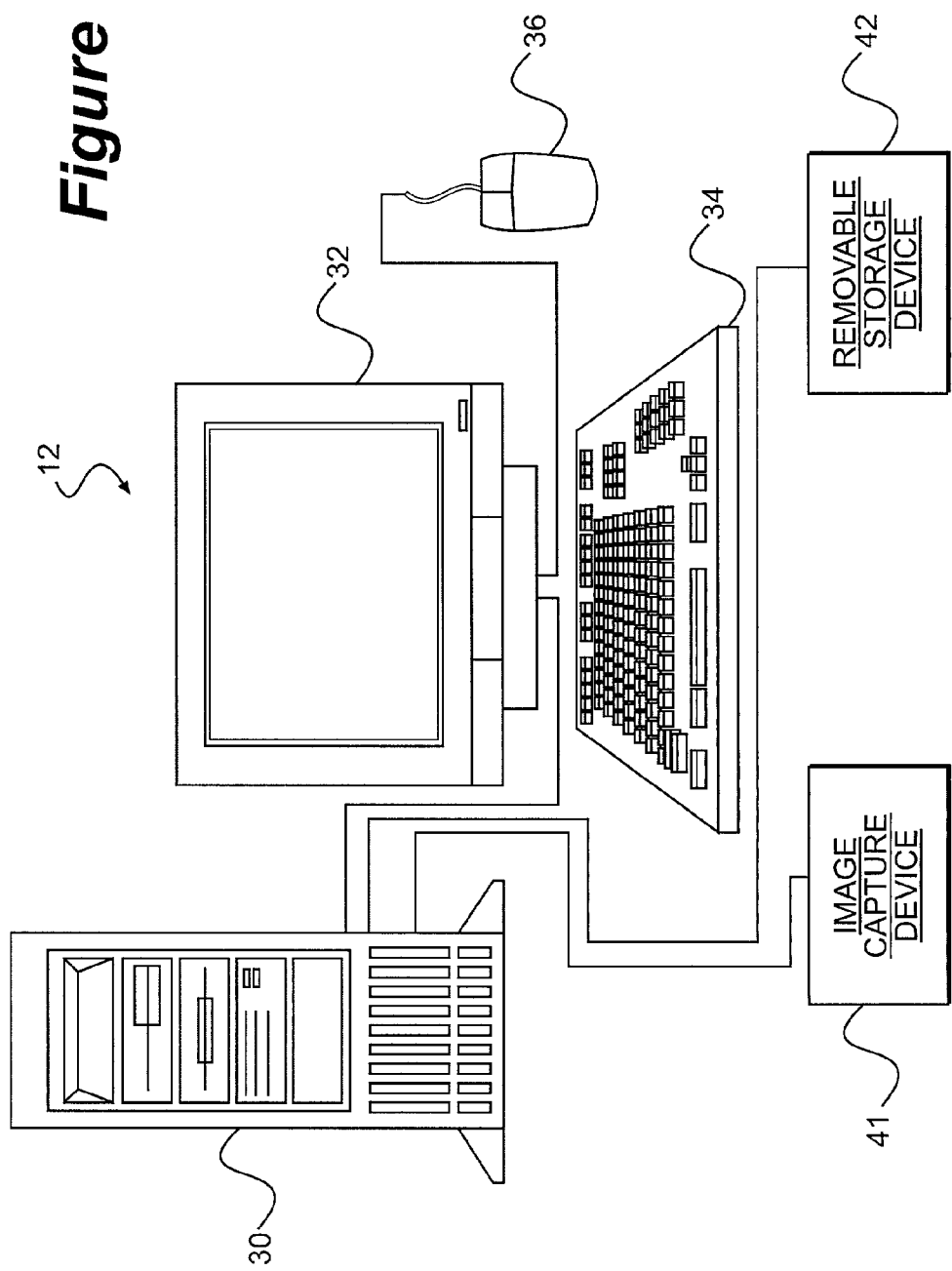
FIG. 12 is a schematic drawing of an exemplary user access device consistent with the present invention.

Referring now to FIG. 12, a user access device may include a computing module 30, a display 32, a keyboard 34, a pointing device 36, such as a mouse, an image capture device 41 and a removable data storage device 42. Although FIG. 12 illustrates an exemplary user access device based on a personal computer platform, the user access device may be implemented using a hand-held device platform or any other type of computing platform. Thus, for example, the various components depicted in FIG. 11 may all be combined in any type of combination to provide a user access device. In other words, the aforementioned description is not meant to be exhaustive; it being understood that the term "user access device," as used herein, may relate to any type of device that may be used by a subject to access (e.g., receive) and/or supply (e.g., transmit) at least some information associated with the method described above. In addition, the invention may be carried out in whole or in part within the environment of FIG. 12.

Figure 13:
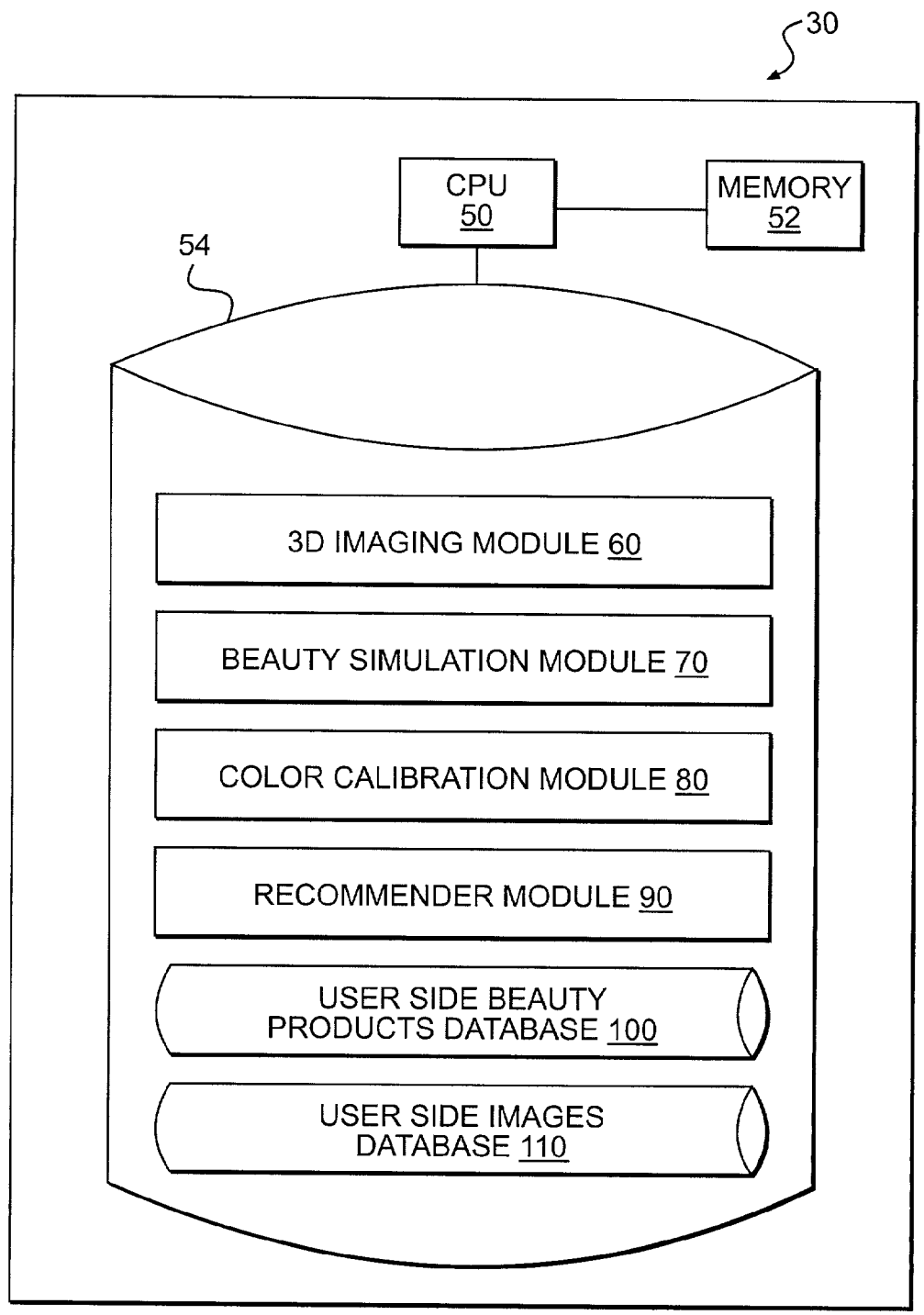
FIG. 13 is a schematic drawing of an exemplary embodiment of a computing module for the user access device of FIG. 12.

FIG. 13 shows an exemplary embodiment of a computing module 30 of the user access device 12 of FIG. 12. Computing module 30 may include at least one CPU 50, at least one memory 52, and at least one storage device 54. Storage device 54, in an exemplary embodiment, may further include a 3D imaging module 60, makeup simulation module 70, color calibration module 80, recommender module 90, user side beauty products database 100, user side images database 110.

Although information used by the system may be generally described as being stored in a storage device, one skilled in the art will appreciate that information may be stored on or read from various computer-readable media, such as secondary storage devices, like hard disks, floppy disks, and CD-ROM; a carrier wave received from a network like the Internet; or other forms of ROM or RAM. In one example, instructions for the beauty module 100 may be downloaded from a remote location. Additionally, it should be noted that the components of the user access device depicted in FIGS. 12 and 13 are merely exemplary. For example, the user access device may contain additional, fewer, and/or differing components.

Figure 14:
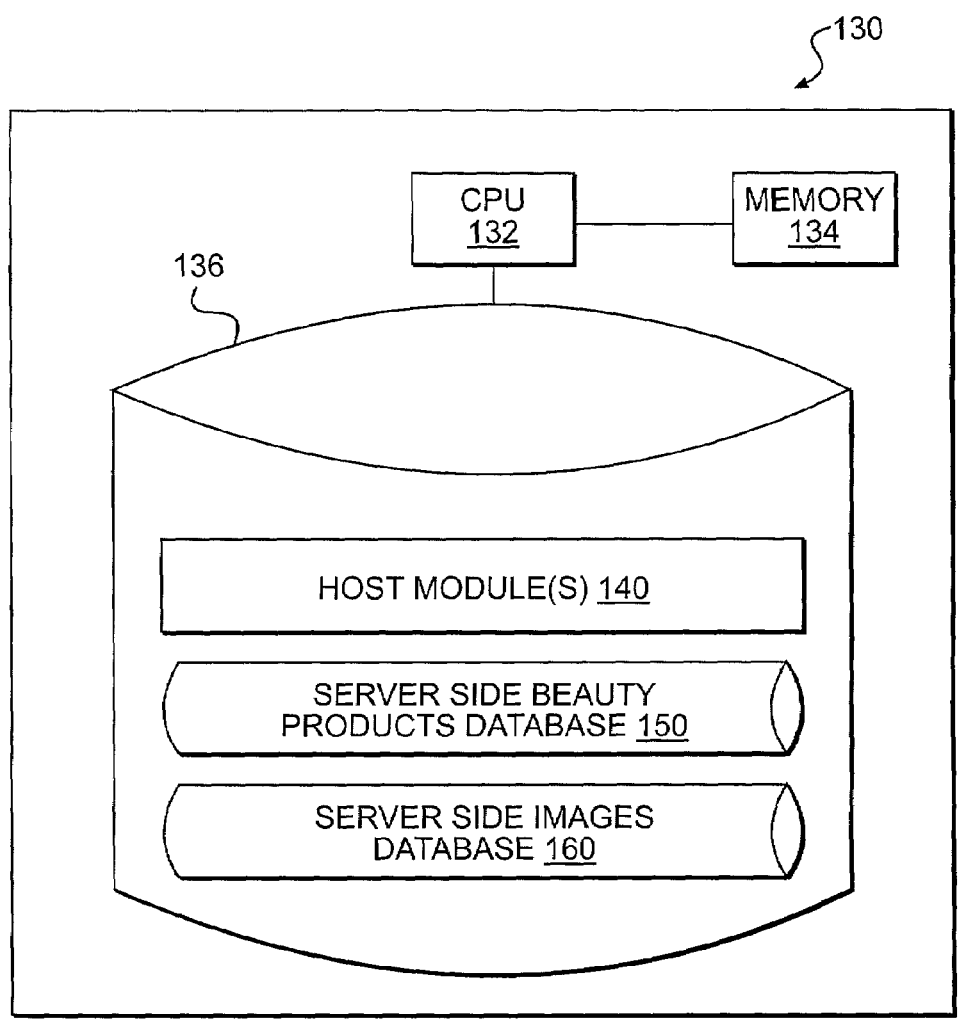
FIG. 14 is a schematic drawing of an exemplary embodiment of a computing module for a host site shown in FIG. 11.

FIG. 14 illustrates an exemplary host site 130. Host site 130 may include at least one CPU 132, at least one memory 134, and at least one storage device 136. Storage device 136, in an exemplary embodiment, may further include host module(s) 140, a server side beauty products database 150, and a server side images database 160. Host module(s) 140 when executed by CPU 132 may interface with the module(s) on the user side. Although not shown, one skilled in the art will appreciate that host module(s) 140 may interface with other components such as a web server software and other Internet-related application and/or networking software to enable communication with communications network 19.

This application may discuss beauty products in connection with use by women. However, it is to be understood that such discussions are for exemplary purposes only. It is to be understood that the invention is equally applicable to all genders, and is not necessarily limited to the beauty industry. It is also to be understood that any functional aspect of the invention can be implemented via any location in the system or network, and data software may be resident at any location either in a network, at a stand-alone site, or on media in the custody and control of a user or subject.

It is to be further understood that the physical mechanisms (e.g. hardware, software, networks, systems) for implementing the methods of the invention are many. Networks, hardware and systems can be configured in a host of ways with software and hardware functionality residing at many alternative locations. In addition, systems other than the exemplary systems disclosed might be used to implement the invention. Therefore, it is to be understood that the methods of the invention are not limited to any particular structure.

Further, methods or portions thereof can be implemented in either an electronic environment, a physical environment, or combinations thereof. Thus, for example, although one or more portions of a method may occur in an electronic environment, a "purchase" portion of the method may occur in a brick and mortar store, or vice versa.

Cross-reference to Concurrently Filed Applications and Global Definitions

This application claims priority on and incorporates by reference the following U.S. Provisional applications: Artificial Intelligence For Use In Cosmetic And Non-Cosmetic Environments, Application No. 60/325,561 (provisional filed Oct. 1, 2001); and Methods And Systems For Cosmetic And Non-Cosmetic Product Selection, Application No. 60/325,559 (provisional filed Oct. 1, 2001).

The following concurrently filed U.S. patent applications are also incorporated herein by reference: Body Image Enhancement, Ser. No. 10/024,480; Methods And Systems For Predicting And/Or Tracking Changes In External Body Conditions, Ser. No. 10/024,354; Methods And Systems For Generating A Prognosis, Ser. No. 10/024,333; Historical Beauty Record, Ser. No. 10/024,622; Identification And Presentation Of Analogous Beauty Case Histories, Ser. No. 10/024,332; Interactive Beauty Analysis, Ser. No. 10/024,481; Feature Extraction In Beauty Analysis, Ser. No. 10/024,495; Simulation Of An Aesthetic Feature On A Facial Image, Ser. No. 10/024,353; Beauty Advisory System And Method, Ser. No. 10/024,496; Virtual Beauty Consultant, Ser. No. 10/024,620; Calibrating Image Capturing, Ser. No. 10/024,334; Use Of Artificial Intelligence In Providing Beauty Advice, Ser. No. 10/024,616; Shop-In-Shop Website Construction, Ser. No. 10/024,352; Early Detection Of Beauty Treatment Progress, Ser. No. 10/024,619; Cosmetic Affinity Indexing, Ser. No. 10/024,356; Systems And Methods For Providing Beauty Guidance, Ser. No. 10/024,621; Methods And Systems Involving Simulated Application Of Beauty Products, Ser. No. 10/024,355; Customized Beauty Tracking Kit, Ser. No. 10/024,351; Body Image Templates With Pre-Applied Beauty Products, Ser. No. 10/024,482; and Image Capture Method, Ser. No. 10/024,651.

To the extent not inconsistent with the invention defined herein, definitions and terminology usage in the above-mentioned concurrently filed applications, the above-mentioned priority applications, and the following global definitions are to be considered in interpreting the language of this patent and the claims herein. Where multiple definitions are provided, they should be considered as a single cumulative definition.

The term "image" may include one or more of two-dimensional and three-dimensional representations. In certain examples consistent with the invention, a plurality of images from different perspectives may be used to construct a three-dimensional image. In a broader sense, only a single image may be used. Depending on the embodiment, the term "image" may include either a visually perceptible image or electronic image data that may be either used to construct a visually perceptible image or to derive information about the subject. The image may be a body image corresponding to an anatomical portion of the subject, and may represent, for example, the subject's entire face, or a portion of the subject's face. The image may be a detailed picture (e.g., a digital image or a photograph) of a portion of the subject's body and/or a topological plot mapping contours of a portion of subject's body. If the image is representative of an external body condition, the image could be either an actual image showing the condition or an image including symbolizations of the condition, for example. The image may be an actual or a simulated image. Simulated images may include wholly or partially generated computer images, images based on existing images, and images based on stored features of a subject.

The term "image capture device", similar terms, and terms representing structures with similar functions may include one or more of a digital camera, webcam, film camera, analog camera, digital video camera, scanner, facsimile machine, copy machine, infrared imager, ultra-sound imaging device, or any other mechanism for acquiring an image of a subject's external body condition, an image of the subject's countenance, an/or an image of the subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image.

The term "capturing (an image)", or any form thereof, refers to the use of an image capture device to acquire an image. "Capturing" may refer to the direct act of using the image capture device to acquire the image. It may also include indirect acts to promote acquisition. To this end, "capturing" may include the indirect acts of providing access to hardware, or to at least one of a client-based algorithm and a server-based algorithm for causing the image capture device to capture an image. This may be accomplished by providing a user with software to aid in the image capture process, or providing the user with access to a network location at which the software resides. Also consistent with certain embodiments of the invention, capturing may include at least one of receiving an instruction from the subject to capture an image, indicating to the subject before the image is captured, and indicating to the subject when the image is captured.

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming and decision tree programming, may also be used to identify conditions. Alternatively, one or more digital filters may be passed through the image for locating specific conditions. These examples are provided for illustrative purposes with the understanding that any image processing technique may be used.

The term "network interface" or similar terms, refer to any mechanism for aiding communications between various nodes or locations in a network. A network interface may include, for example a bus, a modem, or any other input/output structure. A network interface may permit a connection to any network capable of being connected to an input and/or output module located within at least one or more of the following exemplary networks: an Ethernet network, an Internet Protocol network, a telephone network, a radio network, a cellular network, or any mechanism for permitting communication between two or more modes or remote locations. In some invention embodiments, a network interface might also included a user interface.

The term "user interface" may include at least one component such as a keyboard, key pad, mouse, track ball, telephone, scanner, microphone, touch screen, web cam, interactive voice response system (IVR), voice recognition system or any other suitable input mechanism for conveying information. A user interface may also include an input port connected by a wired, optical, or wireless connection for electromagnetic transmissions. In some embodiments, a user interface may include connections to other computer systems to receive the input commands and data therefrom. User interface may further include a data reading device such as a disk drive for receiving input data from and writing data to storage media such as magnetic and optical disks.

As used herein terms such as "external body condition", "skin condition", and "actual condition" refer to conditions of at least one of the skin, teeth, hair, eyebrows, eyelashes, body hair, facial hair, fingernails, and/or toenails, or any other externality. Examples of skin conditions may include elasticity, dryness, cellulitis, sweating, aging, wrinkles, melanoma, exfoliation, desquamation, homogeneity of color, creases, liver spots, clarity, lines, micro-circulation, shininess, softness, smoothness, tone, texture, matitty, hydration, sag, suppleness, stress, springiness, firmness, sebum production, cleanliness, translucency, luminosity, irritation, redness, vasocolation, vasomotion, vasodilation, vasoconstriction, pigmentation, freckles, blemishes, oiliness, pore distribution, pore size, moles, birthmarks, acne, blackheads, whiteheads, pockmarks, warts, pustules, boils, blisters, marks, smudges, specks, psoriasis and other characteristics associated with the subject's skin. Examples of hair conditions may include keratin plug, length, dryness, oiliness, dandruff, pigmentation, thickness, density, root conditions, split ends, hair loss, hair thinning, scales, staging, cleanliness and other properties related to the subject's hair. Examples of fingernail and toenail conditions may include onychomycosis, split nails, delaminating, psoriasis, brilliancy, lines, spots, coloration, gloss, strength, brittleness, thickness, hangnail, length, disease, and other characteristics related to the subject's nails. Other conditions may include, for example, size and proportion of facial features, teeth discoloration, and any other aesthetic-related or physical, physiological, or biological conditions of the user.

"Enabling", "facilitating", and "causing" an action refer to one or more of a direct act of performing the action, and any indirect act of encouraging or being an accessory to the action. Thus, the terms include partnering or cooperating with an entity who performs the action and/or referring commerce to or having commerce referred from an entity who performs the action. Other examples of indirect activity encompassed within the definitions of "enabling", "facilitating", and "causing" may include providing a subject with one or more of tools to knowingly aid in performing the action, providing instructions on how to perform the action, providing prompts or cues to perform the action, or expressly encouraging performance of the action. Indirect activity may also include cooperating with an entity who either directly performs the action or who helps another perform the action. Tools may include software, hardware, or access (either directly, through hyperlink, or some other type of cooperation or partnering) to a network location (e.g., web site) providing tools to aid in performing the action. Thus, phrases such as "enabling access" and "enabling display" do not necessary require that the actor actually access or display anything. For example, the actor may perform the enabling function by affiliating with an entity who performs the action, or by providing instructions, tools, or encouragement for another to do the accessing and displaying.

Forms of the word "displaying" and like terms may also include indirect acts such as providing content for transmission over a network to a display device, regardless of whether the display device is in the custody or control of the sender. Any entity in a chain of delivering information for display performs an act of "displaying", as the term is used herein.

Likewise, the term "providing" includes direct and indirect activities. For example, providing access to a computer program may include at least one of providing access over a network to the computer program, and creating or distributing to the subject a computer program configured to run on the subject's workstation or computer. For example, a first party may direct network traffic to (either through electronic links or through encouragement to visit) a server or web site run by a second party. If the second party maintains a particular piece of software thereon, then it is to be understood that within the meaning of "providing access" as used herein, the first party is said to provide access to the particular software. Or if the first party directs a subject to a second party who in turn ships the particular software to the user, the first party is said to provide the user with access to the particular software. (Of course, in both of the above instances, the second party would also be providing access within the meaning of the phrase as used herein.) "Receiving" may include at least one of acquisition via a network, via verbally communication, via electronic transmission, via telephone transmission, in hard-copy form, or through any other mechanism enabling reception. In addition, "receiving" may occur either directly or indirectly. For example, receipt may occur through a third party acting on another party's behalf, as an agent of another, or in concert with another. Regardless, all such indirect and direct actions are intended to be covered by the term "receiving" as used herein. A received request, for example, may take one of many forms. It may simply be a checked box, clicked button, submitted form or oral affirmation. Or it might be a typed or handwritten textual request. Receiving may occur through an on-line interest form, e-mail, facsimile, telephone, interactive voice response system, or file transfer protocol transmitted electronically over a network at a web site, an internet protocol address, or a network account. A request may be received from a subject for whom information is sought, or an entity acting on the subject's behalf. "Receiving" may involve receipt directly or indirectly through one or more networks and/or storage mediums. Receipt may occur physically such as in hard copy form, via mail delivery or other courier delivery.

Forms of the word "maintain" are used broadly to include gathering, storing, accessing, providing access to, or making something available for access, either directly or indirectly. For example, those who maintain information include entities who provide a link to a site of a third party where the information is stored.

Consistent with the concepts set forth above, all other recited actions such as, for example, obtaining, determining, generating, selecting, applying, simulating, presenting, etc, are inclusive of direct and indirect actions. Thus, for purposes of interpreting the following claims, an entity performs a recited action through either direct or indirect activity. Further examples of indirect activity include sending signals, providing software, providing instructions, cooperating with an entity to have the entity perform the action, outsourcing direct or indirect actions, or serving in any way as an accessory to the specified action.

The term "product" is used to generically refer to tangible merchandise, goods, services, and actions performed. A "beauty product," "beauty care product," "cosmetic product" or similar terms, refer to products (as defined above) for effecting one or more external body conditions, such as conditions of the skin, hair and nails. Examples of tangible merchandise forms of beauty products include cosmetic goods, such as treatment products, personal cleansing products, and makeup products, in any form (e.g., ointments, creams, gels, sprays, supplement, ingesta, inhalants, lotions, cakes, liquids, and powders.)

Examples of services forms of beauty products include hair styling, hair cutting, hair coloring, hair removal, skin treatment, make-up application, and any other offering for aesthetic enhancement. Examples of other actions performed include massages, facial rubs, deep cleansings, applications of beauty product, exercise, therapy, or any other action effecting the external body condition whether performed by a professional, the subject, or an acquaintance of the subject.

The following is exemplary and non-exhaustive listing of a few beauty products-scrubs, rinses, washes, moisturizers, wrinkle removers, exfoliates, toners, cleansers, conditioners, shampoos, cuticle creams, oils, and anti-fungal substances, anti-aging products, anti-wrinkle products, anti-freckle products, skin conditioners, skin toners, skin coloring agents, tanners, bronzers, skin lighteners, hair coloring, hair cleansing, hair styling, elasticity enhancing products, agents, blushes, mascaras, eyeliners, lip liners, lipsticks, lip glosses, eyebrow liners, eye shadows, nail polishes, foundations, concealers, dental whitening products, cellulite reduction products, hair straighteners and curlers, and weight reduction products. A beauty care treatment regimen may involve the administration of one or more products, as defined above.

The terms "beauty advice", "beauty guidance", and similar terms are used interchangeably to refer to the provision of beauty related information to a subject. Advice or guidance includes one or more of beauty product recommendations (e.g., cosmetic product recommendations for products to treat conditions the subject is prompted to evaluate), remedial measures, preventative measures, predictions, prognoses, price and availability information, application and use information, suggestions for complementary products, lifestyle or dietary recommendations, or any other information intended to aid a subject in a course of future conduct, to aid a subject in understanding past occurrences, to reflect information about some future occurrences related to the subject's beauty or to aid a subject in understanding beauty products, as defined above.

The term "network" may include a public network such as the Internet or a telephony network, a private network, a virtual private network, or any other mechanism for enabling communication between two or more nodes or locations. The network may include one or more of wired and wireless connections. Wireless communications may include radio transmission via the airwaves, however, those of ordinary skill in the art will appreciate that various other communication techniques can be used to provide wireless transmission including infrared line of sight, cellular, microwave, satellite, blue-tooth packet radio and spread spectrum radio. Wireless data may include, but is not limited to, paging, text messaging, e-mail, Internet access and other specialized data applications specifically excluding or including voice transmission.

In some instances consistent with the invention, a network may include a courier network (e.g. postal service, United Parcel Service, Federal Express, etc.). Other types of networks that are to be considered within the scope of the invention include local area networks, metropolitan area networks, wide area networks, ad hoc networks, or any mechanism for facilitating communication between two nodes or remote locations.

"Artificial intelligence" (AI) is used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, or soft computing. Employing any computationally intelligent techniques, the AI engine may learn to adapt to unknown or changing environment for better performance. AI engines may be implemented or provided with a wide variety of components or systems, including one or more of the following: central processing units, co-processors, memories, registers, or other data processing devices and subsystems.

AI engines may be trained based on input such as product information, expert advice, user profile, or data based on sensory perceptions. Using input an AI engine may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, or recording learning. As a result of the training, AI engine may learn to modify its behavior in response to its environment, and obtain knowledge. Knowledge may represent any information upon which AI engine may determine an appropriate response to new data or situations. Knowledge may represent, for example, relationship information between two or more products. Knowledge may be stored in any form at any convenient location, such as a database.

Since AI engine may learn to modify its behavior, information describing relationships for a universe of all combinations of products may not need to be maintained by the AI engine or any other component of the system.

"Personal information", "subject specific information", "user specific information", "user profile", "personal characteristics", "personal attributes", "profile information", and like terms (collectively referred to in this section as "personal information") may broadly encompass any information about the subject or user. Such information may, for example, fall within categories such as physical characteristics, fashion preferences, demographics, nutritional information, cosmetic usage information, medical history information, environmental information, beauty product usage information, lifestyle, and may include information such as name; age; birth date; height; weight; ethnicity; eating habits; vacation patterns; geographic location of the individual's residence, location, or work; work habits; sleep habits; toiletries used; exercise habits; relaxation habits; beauty care habits; smoking and drinking habits; sun exposure habits; use of sunscreen; propensity to tan; number of sunburns and serious sunburns; dietary restrictions; dietary supplements or vitamins used; diagnosed conditions affecting the external body, such as melanoma; an image, such as a picture or a multimedia file of the subject; facial feature characteristics; family history information such as physical characteristics information about relatives of the subject (e.g., premature balding, graying, wrinkles, etc.); external body condition (as defined previously); color preferences, clothing style preferences, travel habits; entertainment preferences; fitness information; adverse reactions to products, compounds, or elements (e.g., sun exposure); body chemistry, use of prior beauty care products and their effectiveness; purchasing, shopping, and browsing habits; hobbies; marital status; whether the subject is a parent; country of residence; region of residence; birth country and region; religious affiliation; political affiliation; whether the subject is an urban dweller suburban dweller or rural area dweller; size of urban area in which the subject lives; whether the subject is retired; annual income, sexual preference, or any other information reflecting habits, preferences, or affiliations of the subject.

Personal information may also include information electronically gleaned by tracking the subject's electronic browsing or purchasing habits, or as the result of cookies maintained on the subject's computer, responses to surveys, or any other mechanism providing information related to the subject. In addition, personal information may be gathered through non-electronic mechanisms such as hard copy surveys, personal interviews, or consumer preference polls.

"Complementary" and "complementary product" refers to one or more of physical, physiological, biologically, and aesthetic compatibility. A product may be complementary with one or more of another product, a group of products, or a subject. In that latter instance, whether a product is considered "complementary" may be a function of personal information of the subject. Thus, for example a product may be complementary if it is unlikely to cause an adverse allergic reaction; if it physically blends well with another product; or if it is aesthetically consistent with the subject or one or more other products. Aesthetic compatibly may refer to the fact that two products are aesthetically appealing (or do not clash) when worn together. The identification of a complementary product may also be based on product characteristics, user preferences, survey data, or expert advice.

As used herein, the words "may" and "may be" are to be interpreted in an open-ended, non-restrictive manner. At minimum, "may" and "may be" are to be interpreted as definitively including structure or acts recited. Further, the word "or" is to be interpreted in the conjunctive and the disjunctive.

While flow charts presented herein illustrate a series of sequential blocks for exemplary purposes, the order of blocks is not critical to the invention in its broadest sense. Further, blocks may be omitted and others added without departing from the spirit of the invention. Also, the invention may include combinations of features described in connection with differing embodiments.

Although a focus of the disclosure may be on server-side methods, it is nevertheless to be understood that the invention includes corresponding client-side methods, software, articles of manufacture, and computer readable media, and that computer readable media can be used to store instructions for some or all of the methods described herein. Further, it is to be understood that disclosed structures define means for implementing the functionality described herein, and that the invention includes such means for performing the disclosed functions.

In the foregoing Description of Exemplary Embodiments, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Description of the Exemplary Embodiments, with each claim standing on its own as a separate embodiment of the invention.

What is claimed is:

1. A method of analyzing an external body condition using a three-dimensional facial image, the method comprising:
providing a computer system, wherein the computer system comprises a computer-readable medium containing instructions for execution by at least one processor;
constructing a three-dimensional facial image based on at least one captured image of a subject's face, wherein the at least one captured image reflects at least one external body condition;
processing the three-dimensional facial image to enable a beauty analysis;
analyzing the at least one external body condition via the three-dimensional facial image;
selecting a beauty product for affecting the at least one external body condition based on the analyzing; and
displaying, on a display device, simulated effect of the beauty product on the external body condition via the three-dimensional facial image.

2. The method of claim 1, wherein the processor facilitates a computer graphics technique, and wherein constructing a three-dimensional facial image comprises constructing a three-dimensional facial image based on the computer graphics technique.

3. The method of claim 2, wherein providing a computer system comprises maintaining the computer system as a server, and providing the subject with an access to the server.

4. The method of claim 1, wherein the processor facilitates an image processing technique, and wherein processing the three-dimensional facial image comprises processing the three-dimensional facial image based on the image processing technique.

5. The method of claim 4, wherein the image processing technique comprises at least one of binarization, image partitioning, Fourier transforms, fast Fourier transforms (FFTs), and discrete cosine transforms.

6. The method of claim 4, wherein the image processing technique is applied to enable a beauty analysis.

7. The method of claim 1, wherein processing the three-dimensional facial image comprises identifying the at least one external body condition in the three-dimensional facial image.

8. The method of claim 1, wherein the beauty product comprises a make-up product.

9. The method of claim 1, further comprising displaying the three-dimensional facial image in a plurality of differing virtual perspectives.

10. The method of claim 1, wherein constructing a three-dimensional facial image further comprises:
transmitting the at least one captured image to a location remote from the subject, and
constructing a three-dimensional facial image at the remote location.

11. The method of claim 1, further comprising capturing on an image capturing device the at least one image of the subject's face.

12. The method of claim 1, wherein processing the three-dimensional facial image comprises processing the three-dimensional facial image at a location remote from the subject.

13. The method of claim 1, wherein constructing a three-dimensional facial image comprises constructing a three-dimensional facial image using a plurality of facial images of the subject.

14. The method of claim 1, wherein constructing a three-dimensional facial image comprises constructing a three-dimensional facial image using the at least one image of the subject's face and a three-dimensional frame.

15. The method of claim 1, wherein the analyzing the at least one external body condition comprises analyzing the at least one external body condition at a location remote from a location of the subject.

16. The method of claim 1, wherein displaying simulated effect of the beauty product comprises displaying a time-lapsed simulation of the three-dimensional facial image.

17. The method of claim 1, wherein constructing a three-dimensional facial image using at least one captured image of a subject's face comprises applying the at least one captured image in a virtual manner on a three-dimensional frame.

18. The method of claim 17, wherein applying the at least one captured image comprises applying the at least one captured image in a virtual manner on a three-dimensional frame that is in the form of a virtual wire mesh.

19. The method of claim 17, further comprising generating the three-dimensional frame based on stored information.

20. The method of claim 17, further comprising generating the three-dimensional frame based on inputted information.

21. The method of claim 1, wherein the three-dimensional facial image reflects the at least one external body condition using a facial model.

22. The method of claim 1, further comprising calibrating the three-dimensional facial image to address a perceived difference between the three-dimensional facial image and the subject's face.

23. The method of claim 1, further comprising color-calibrating the three-dimensional facial image to simulate the subject's actual face.

24. The method of claim 23, wherein displaying simulated effect of the beauty product on the external body condition via the three-dimensional facial image comprises displaying simulated effect of the beauty product on the color-calibrated three-dimensional facial image.

25. The method of claim 23, wherein color-calibrating further comprises comparing a displayed color of the three-dimensional facial image with an actual color of an actual body region to color-calibrate the three-dimensional facial image.

26. The method of claim 1, wherein analyzing the external body condition via the three-dimensional facial image includes determining an extent and severity of the at least one external body condition.

27. The method of claim 1, wherein constructing a three-dimensional facial image further comprises adding a dimensional effect to the three-dimensional facial image.

28. The method of claim 1, wherein constructing a three-dimensional facial image further comprises adding a lighting effect to the three-dimensional facial image.

29. The method of claim 28, wherein adding a lighting effect comprises applying color homogenously to the facial image while modifying at least one of hue, tint, and shade based on a position of a virtual lighting source.

30. The method of claim 1, wherein constructing a three-dimensional facial image comprises constructing a three-dimensional facial image that includes selectable portions that, when selected, are displayed in two-dimensional form.

31. The method of claim 1, wherein constructing a three-dimensional facial image comprises constructing a two-dimensional facial image that includes selectable portions that, when selected, are displayed in three-dimensional form.

32. The method of claim 1, wherein the processor facilitates a computer graphics technique, and wherein processing the three-dimensional facial image comprises modifying, using the computer graphic technique, the three-dimensional facial image to reflect evolution of the external body condition over time.

33. The method of claim 1, further comprising receiving, using the processor, a feedback from the subject on the beauty product.

34. The method of claim 33, further comprising selecting, using the processor, a second beauty product based on the feedback.

35. The method of claim 34, further comprising displaying, on the display device, simulated effect of the beauty product and the second beauty product via the three-dimensional facial image.

36. The method of claim 1, further comprising providing, using the processor, the subject with information related to purchasing the beauty product.

37. The method of claim 1, wherein the processor facilitates an analytic technique, and wherein analyzing the at least one external body condition comprises analyzing the at least one external body condition based on the analytic technique.

38. The method of claim 37, wherein the analytic technique comprises at least one of statistical analysis, modeling, textual analysis, collaborative filtering, and artificial intelligence.

39. The method of claim 1, wherein selecting a beauty product comprises selecting a beauty product based on personal information of the subject, wherein the personal information comprises at least one of physical attributes, lifestyle information, type of look, and personal preferences.

40. A computer-readable medium containing instructions for causing a computer to perform a method of analyzing an external body condition using a three-dimensional facial image, the method comprising:
constructing a three-dimensional facial image based on at least one captured image of a subject's face, wherein the at least one captured image reflects at least one external body condition;
processing the three-dimensional facial image to enable a beauty analysis;
analyzing the at least one external body condition via the three-dimensional facial image;
selecting a beauty product for affecting the at least one external body condition based on the analyzing; and
displaying, on a display device, simulated effect of the beauty product on the external body condition via the three-dimensional facial image.

41. A computer system for use in analyzing an external body condition using a three-dimensional facial image, the system comprising:
a processor; and
a memory for storing instructions for the processor to perform a method comprising:
constructing a three-dimensional facial image based on at least one captured image of a subiect's face, wherein the at least one captured image reflects at least one external body condition;
processing the three-dimensional facial image to enable a beauty analysis;
analyzing the at least one external body condition via the three-dimensional facial image;
selecting a beauty product for affecting the at least one external body condition based on the analyzing; and
displaying, on a display device, simulated effect of the beauty product on the external body condition via the three-dimensional facial image.

* * * * *

UNITED STATES PATENT AND TRADEMARK OFFICE
CERTIFICATE OF CORRECTION

PATENT NO. : 7,634,103 B2  
APPLICATION NO. : 10/024615  
DATED : December 15, 2009  
INVENTOR(S) : Gilles Rubinstenn et al.

It is certified that error appears in the above-identified patent and that said Letters Patent is hereby corrected as shown below:

Claim 15, column 28, line 18, "wherein the analyzing" should read --wherein analyzing--.

Claim 40, column 30, line 9, "subiect's" should read --subject's--.

Claim 41, column 30, line 28, "subiect's" should read --subject's--.

Signed and Sealed this

Second Day of March, 2010

David J. Kappos
*Director of the United States Patent and Trademark Office*